(12) United States Patent
Oberhauser et al.

(10) Patent No.: US 7,419,976 B2
(45) Date of Patent: Sep. 2, 2008

(54) DIAZEPANES DERIVATIVES USEFUL AS IFA INHIBITORS

(75) Inventors: Berndt Oberhauser, Vienna (AT); Josef G Meingassner, Perchtoldsdorf (AT)

(73) Assignee: Novartis AG, Basel (CH)

( * ) Notice: Subject to any disclaimer, the term of this patent is extended or adjusted under 35 U.S.C. 154(b) by 4 days.

(21) Appl. No.: 10/541,183

(22) PCT Filed: Jan. 22, 2004

(86) PCT No.: PCT/EP2004/000514

§ 371 (c)(1),
(2), (4) Date: Jun. 30, 2005

(87) PCT Pub. No.: WO2004/065382

PCT Pub. Date: Aug. 5, 2004

(65) Prior Publication Data

US 2006/0148780 A1     Jul. 6, 2006

(30) Foreign Application Priority Data

Jan. 23, 2003   (GB) ................. 0301561.7
Oct. 13, 2003   (GB) ................. 0323976.1

(51) Int. Cl.
*C07D 403/06*   (2006.01)
*C07D 403/14*   (2006.01)
*A61K 31/5513*  (2006.01)
*A61P 37/08*    (2006.01)

(52) U.S. Cl. ..................... 514/218; 540/492
(58) Field of Classification Search ......... 540/492; 514/218

See application file for complete search history.

(56) References Cited

U.S. PATENT DOCUMENTS 6,399,599 B1 *  6/2002  Albert et al. ............... 514/218

FOREIGN PATENT DOCUMENTS

| WO | 01/27102  | 4/2001 |
| WO | 02/28842  | 4/2002 |
| WO | 02/059114 | 8/2002 |

OTHER PUBLICATIONS

Sompong Wattanasin, "1-4-Diazepane-2-ones as novel inhibitors of LFA-1", Bioorganic and Medicinal Chemistry Letters, vol. 13, No. 3, pp. 499-502 (2002).

* cited by examiner

*Primary Examiner*—Bruck Kifle

(57) ABSTRACT

Pharmaceutically active diazepanes, e.g. useful for treating disorders or diseases mediated by LFA-1/ICAM-1, LFA-1/ICAM-2, LFA-1/ICAM-3 or LFA-1/JAM-1 interactions.

22 Claims, No Drawings

DIAZEPANES DERIVATIVES USEFUL AS IFA INHIBITORS

The present invention relates to pharmaceutically active diazepanes.

In one aspect the present invention provides a compound of formula

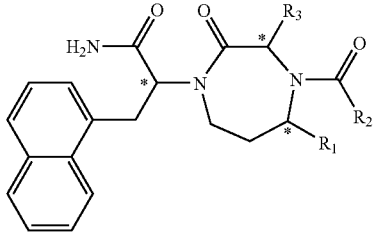

e.g. including a compound of formula

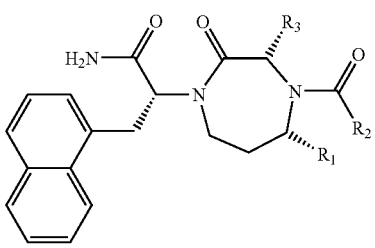

wherein
$R_1$ is $(C_{1-4})$alkyl, e.g. methyl
$R_2$ is unsubstituted $(C_{1-4})$alkyl, e.g. methyl, or $(C_{1-4})$alkyl substituted by unsubstituted or substituted
  $(C_{6-18})$aryl, e.g. phenyl or
  $(C_{6-18})$aryl, e.g. phenyl, annelated with heterocyclyl having 5 or 6 ring members and 1 to 4 heteroatoms selected from N, O, S,
  e.g. which aryl or aryl annelated with heterocyclyl is one or morefold substituted by
    halogen,
    halo$(C_{1-6})$alkyl,
    $(C_{1-6})$alkoxy,
    cyano,
    amino,
$R_3$ is $(C_{6-18})$aryl, e.g. phenyl, one or morefold substituted by
    halogen,
    halo$(C_{1-6})$alkyl,
    halo$(C_{1-6})$alkoxy,
    cyano,
    phenyl,
    heterocyclyl having 5 to 6 ring members and 1 to 4 heteroatoms selected from N, O, S, e.g. aromatic heterocyclyl, such as pyrimidinyl.

Preferably in a compound of formula I
$R_1$ is methyl,
$R_2$ is methyl or
  methyl substituted by
    quinolinyl,
    benzo[1,3]dioxolyl,
    phenyl phenyl one or morefold substituted by halogen, halo$(C_{1-4})$alkyl, $(C_{1-4})$alkoxy, cyano, amino, dimethylamino, carboxy$(C_{1-2})$alkylcarbonylamino, amino$(C_{1-2})$alkylcarbonylamino, $(C_{2-4})$alkylenecarbonylamino, heterocyclylcarbonyl$(C_{1-2})$alkylcarbonylamino, wherein heterocyclyl has 6 ring members and 2 heteroatoms selected from N, O such as piperazinyl, morpholinyl, $R_3$ is phenyl one or morefold, e.g. 1- to 3-fold, substituted by
    halogen,
    halo$(C_{1-2})$alkyl, e.g. $CF_3$;
    halo$(C_{1-2})$alkoxy, e.g. $OCF_3$;
    cyano,
    phenyl,
    heterocyclyl, including aromatic, having 6 ring members and 2 nitrogen heteroatoms, such as pyrimidinyl.

In another aspect the present invention provides a compound of formula I wherein
$R_1$ is methyl,
$R_2$ is methyl substitued by quinolin-6-yl,
$R_3$ is phenyl one or morefold, e.g. 1- or 2-fold, substituted by
    halogen, e.g. fluoro, chloro, bromo;
    halo$(C_{1-2})$alkyl, e.g. $CF_3$,
    halo$(C_{1-2})$alkoxy, e.g. $OCF_3$,
    phenyl,
    aromatic heterocyclyl having 6 ring members and 2 nitrogen heteroatoms, e.g. pyrimidin-5-yl.

In another aspect the present invention provides a compound of formula I wherein
$R_1$ is methyl,
$R_2$ is methyl substituted by benzo[1,3]dioxol-5-yl,
$R_3$ is phenyl one or morefold, e.g. 1- or 2-fold, substituted by
    halogen, e.g. fluoro or chloro;
    halo$(C_{1-2})$alkyl, e.g. $CF_3$;
    halo$(C_{1-2})$alkoxy, e.g. $OCF_3$;
    cyano.

In another aspect the present invention provides a compound of formula I wherein
$R_1$ is methyl,
$R_2$ is methyl substituted by phenyl or methyl substituted by phenyl one or morefold, e.g. 1 to 3-fold, substituted by
    halogen, e.g. chloro;
    halo$(C_{1-2})$alkyl, e.g. $CF_3$;
    $(C_{1-2})$alkoxy, e.g. methoxy;
    cyano,
    amino,
    dimethylamino,
    carboxy$(C_{1-2})$alkylcarbonylamino,
    amino$(C_{1-2})$alkylcarbonylamino,
    ethenylcarbonyl amino
    heterocyclylcarbonyl-$(C_{1-2})$alkylcarbonylamino, wherein heterocyclyl has 6 ring members and 2 heteroatoms selected from N, O, S, preferably from N or O, e.g. piperazin-1-yl or morpholin-4-yl,
$R_3$ is phenyl substituted one or morefold by
    halogen, e.g. chloro or fluoro;
    halo$(C_{1-2})$alkyl, e.g. $CF_3$;
    halo$(C_{1-2})$alkoxy, e.g. $OCF_3$;
    cyano.

In another aspect the present invention provides a compound of formula I wherein
$R_1$ is methyl,
$R_2$ is methyl,
$R_3$ is phenyl substituted by halogen, e.g. chloro.

In another aspect the present invention provides a compound selected from the group consisting of

- 2-[3-(3-Fluoro-phenyl)-5-methyl-2-oxo-4-(quinolin-6-yl-acetyl)-[1,4]diazepan-1-yl]-3-naphthalen-1-yl-propionamide, e.g. (R)-2-[3,5-cis-3-(3-Fluoro-phenyl)-5-methyl-2-oxo-4-(quinolin-6-yl-acetyl)-[1,4]diazepan-1-yl]-3-naphthalen-1-yl-propionamide,
- 2-[5-Methyl-2-oxo-4-(quinolin-6-yl-acetyl)-3-(3-trifluoromethyl-phenyl)-[1,4]diazepan-1-yl]-3-naphthalen-1-yl-propionamide, e.g. (R)-2-[3,5-cis-5-Methyl-2-oxo-4-(quinolin-6-yl-acetyl)-3-(3-trifluoromethyl-phenyl)-[1,4]diazepan-1-yl]-3-naphthalen-1-yl-propionamide,
- 2-[3-(4-Fluoro-phenyl)-5-methyl-2-oxo-4-(quinolin-6-yl-acetyl)-[1,4]diazepan-1-yl]-3-naphthalen-1-yl-propionamide, e.g. (R)-2-[3,5-cis-3-(4-Fluoro-phenyl)-5-methyl-2-oxo-4-(quinolin-6-yl-acetyl)-[1,4]diazepan-1-yl]-3-naphthalen-1-yl-propionamide,
- 2-[3-(2-Fluoro-phenyl)-5-methyl-2-oxo-4-(quinolin-6-yl-acetyl)-[1,4]diazepan-1-yl]-3-naphthalen-1-yl-propionamide, e.g. (R)-2-[3,5-cis-3-(2-Fluoro-phenyl)-5-methyl-2-oxo-4-(quinolin-6-yl-acetyl)-[1,4]diazepan-1-yl-3-naphthalen-1-yl-propionamide,
- 2-[3-(3-Bromo-phenyl)-5-methyl-2-oxo-4-(2-quinolin-6-yl-acetyl)-[1,4]diazepan-1-yl]-3-naphthalen-1-yl-propionamide, e.g. 2-[3,5-cis-3-(3-Bromo-phenyl)-5-methyl-2-oxo-4-(2-quinolin-6-yl-acetyl)-[1,4]diazepan-1-yl-3-naphthalen-1-yl-propionamide,
- 2-[3-Biphenyl-3-yl-5-methyl-2-oxo-4-(2-quinolin-6-yl-acetyl)-[1,4]diazepan-1-yl]-3-naphthalen-1-yl-propionamide,
- 2-[3-(3-Chloro-phenyl)-5-methyl-2-oxo-4-(2-quinolin-6-yl-acetyl)-[1,4]diazepan-1-yl]-3-naphthalen-1-yl-propionamide, e.g. (R)-2-[(3S,5R)-3-(3-Chloro-phenyl)-5-methyl-2-oxo-4-(2-quinolin-6-yl-acetyl)-[1,4]diazepan-1-yl]-3-naphthalen-1-yl-propionamide,
- 2-[3-(3,5-Dichloro-phenyl)-5-methyl-2-oxo-4-(2-quinolin-6-yl-acetyl)-[1,4]diazepan-1-yl]-3-naphthalen-1-yl-propionamide, e.g. (R)-2-[(3S,5R)-3-(3,5-Dichloro-phenyl)-5-methyl-2-oxo-4-(2-quinolin-6-yl-acetyl)-[1,4]diazepan-1-yl]-3-naphthalen-1-yl-propionamide,
- 2-[3-(4-Chloro-3-trifluoromethyl-phenyl)-5-methyl-2-oxo-4-(2-quinolin-6-yl-acetyl)-[1,4]diazepan-1-yl]-3-naphthalen-1-yl-propionamide, e.g. (R)-2-[(3S,5R)-3-(4-Chloro-3-trifluoromethyl-phenyl)-5-methyl-2-oxo-4-(2-quinolin-6-yl-acetyl)-[1,4]diazepan-1-yl]-3-naphthalen-1-yl-propionamide,
- 2-[3-(3-Chloro-4-fluoro-phenyl)-5-methyl-2-oxo-4-(2-quinolin-6-yl-acetyl)-[1,4]diazepan-1-yl]-3-naphthalen-1-yl-propionamide, e.g. (R)-2-[(3S,5R)-3-(3-Chloro-4-fluoro-phenyl)-5-methyl-2-oxo-4-(2-quinolin-6-yl-acetyl)-[1,4]diazepan-1-yl]-3-naphthalen-1-yl-propionamide,
- 2-[5-Methyl-2-oxo-4-(2-quinolin-6-yl-acetyl)-3-(2-trifluoromethyl-phenyl)-[1,4]diazepan-1-yl]-3-naphthalen-1-yl-propionamide, e.g. (R)-2-[(3S,5R)-5-Methyl-2-oxo-4-(2-quinolin-6-yl-acetyl)-3-(2-trifluoromethyl-phenyl)-[1,4]diazepan-1-yl]-3-naphthalen-1-yl-propionamide,
- 2-[3(3,4-Difluoro-phenyl)-5-methyl-2-oxo-4-(2-quinolin-6-yl-acetyl)-[1,4]diazepan-1-yl]-3-naphthalen-1-yl-propionamide, e.g. (R)-2-[(3S,5R)-3-(3,4-Difluoro-phenyl)-5-methyl-2-oxo-4-(2-quinolin-6-yl-acetyl)-[1,4]diazepan-1-yl]-3-naphthalen-1-yl-propionamide,
- 2-[3-(3-Cyano-phenyl)-5-methyl-2-oxo-4-(2-quinolin-6-yl-acetyl)-[1,4]diazepan-1-yl]-3-naphthalen-1-yl-propionamide, e.g. (R)-2-[(3S,5R)-3-(3-Cyano-phenyl)-5-methyl-2-oxo-4-(2-quinolin-6-yl-acetyl)-[1,4]diazepan-1-yl]-3-naphthalen-1-yl-propionamide,
- 2-[5-Methyl-2-oxo-3-(3-pyrimidin-5-yl-phenyl)-4-(2-quinolin-6-yl-acetyl)-[1,4]diazepan-1-yl]-3-naphthalen-1-yl-propionamide, e.g. (R)-2-[5-Methyl-2-oxo-3-(3-pyrimidin-5-yl-phenyl)-4-(2-quinolin-6-yl-acetyl)-[1,4]diazepan-1-yl]-3-naphthalen-1-yl-propionamide,
- 2-[5-Methyl-2-oxo-4-(2-quinolin-6-yl-acetyl)-3-(3-trifluoromethoxy-phenyl)-[1,4]diazepan-1-yl]-3-naphthalen-1-yl-propionamide, e.g. (R)-2-[(3S,5R)-5-Methyl-2-oxo-4-(2-quinolin-6-yl-acetyl)-3-(3-trifluoromethoxy-phenyl)-[1,4]diazepan-1-yl]-3-naphthalen-1-yl-propionamide,
- 2-[4-(2-Benzo[1,3]dioxol-5-yl-acetyl)-3-(3-fluoro-phenyl)-5-methyl-2-oxo-[1,4]diazepan-1-yl]-3-naphthalen-1-yl-propionamide, e.g. (R)-2-[4-(2-Benzo[1,3]dioxol-5-yl-acetyl)-3,5-cis-3-(3-fluoro-phenyl)-5-methyl-2-oxo-[1,4]diazepan-1-yl]-3-naphthalen-1-yl-propionamide,
- 2-[4-(2-Benzo[1,3]dioxol-5-yl-acetyl)-3-(3-chloro-phenyl)-5-methyl-2-oxo-(1,4]diazepan-1-yl]-3-naphthalen-1-yl-propionamide, e.g. (R)-2-[(3S,5R)-4-(2-Benzo[1,3]dioxol-5-yl-acetyl)-3-(3-chloro-phenyl)-5-methyl-2-oxo-[1,4]diazepan-1-yl]-3-naphthalen-1-yl-propionamide,
- 2-[4-(2-Benzo[1,3]dioxol-5-yl-acetyl)-5-methyl-2-oxo-3-(3-trifluoromethyl-phenyl)-[1,4]diazepan-1-yl]-3-naphthalen-1-yl-propionamide, e.g. (R)-2-[(3S,5R)-4-(2-Benzo[1,3]dioxol-5-yl-acetyl)-5-methyl-2-oxo-3-(3-trifluoromethyl-phenyl)-[1,4]diazepan-1-yl]-3-naphthalen-1-yl-propionamide,
- 2-[4-(2-Benzo[1,3]dioxol-5-yl-acetyl)-3-(3-chloro-4-fluoro-phenyl)-5-methyl-2-oxo-[1,4]diazepan-1-yl]-3-naphthalen-1-yl-propionamide, e.g. (R)-2-[(3S,5R)-4-(2-Benzo[1,3]dioxol-5-yl-acetyl)-3-(3-chloro-4-fluoro-phenyl)-5-methyl-2-oxo-[1,4]diazepan-1-yl]-3-naphthalen-1-yl-propionamide,
- 2-[4-(2-Benzo[1,3]dioxol-5-yl-acetyl)-3-(3-cyano-phenyl)-5-methyl-2-oxo-[1,4]diazepan-1-yl]-3-naphthalen-1-yl-propionamide, e.g. (R)-2-[(3S,5R)-4-(2-Benzo[1,3]dioxol-5-yl-acetyl)-3-(3-cyano-phenyl)-5-methyl-2-oxo-[1,4]diazepan-1-yl]-3-naphthalen-1-yl-propionamide,
- 2-[4-(2-Benzo[1,3]dioxol-5-yl-acetyl)-5-methyl-2-oxo-3-(3-trifluoromethoxy-phenyl)-[1,4]diazepan-1-yl]-3-naphthalen-1-yl-propionamide, e.g. (R)-2-[(3S,5R)-4-(2-Benzo[1,3]dioxol-5-yl-acetyl)-5-methyl-2-oxo-3-(3-trifluoromethoxy-phenyl)-[1,4]diazepan-1-yl]-3-naphthalen-1-yl-propionamide,
- 2-[3-(3-Chloro-phenyl)-5-methyl-2-oxo-4-phenylacetyl-[1,4]diazepan-1-yl]-3-naphthalen-1-yl-propionamide, e.g. (R)-2-[(3S,5R-3-(3-Chloro-phenyl)-5-methyl-2-oxo-4-phenylacetyl-[1,4]diazepan-1-yl]-3-naphthalen-1-yl-propionamide,
- 2-[3-(3-Fluoro-phenyl)-5-methyl-2-oxo-4-[(3-trifluoromethyl-phenyl)-acetyl]-[1,4]diazepan-1-yl]-3-naphthalen-1-yl-propionamide, e.g. (R)-2-{3,5-cis-3-(3-Fluoro-phenyl)-5-methyl-2-oxo-4-[(3-trifluoromethyl-phenyl)-acetyl]-[1,4]diazepan-1-yl}-3-naphthalen-1-yl-propionamide,
- 2-{3-Biphenyl-4-yl-5-methyl-2-oxo-4-[2-(2,3,6-trichloro-phenyl)-acetyl]-[1,4]diazepan-1-yl}-3-naphthalen-1-yl-propionamide, e.g. 3,5-cis-2-{3-Biphenyl-4-yl-5-methyl-2-oxo-4-[2-(2,3,6-trichloro-phenyl)-acetyl]-[1,4]diazepan-1-yl]3-naphthalen-1-yl-propionamide, 2-[4-[2-(4-Cyano-phenyl)-acetyl]-3-(3,4-difluoro-phenyl)-5-methyl-2-oxo-[1,4]diazepan-1-yl]-3-naphthalen-1-yl-propionamide, e.g. (R)-2-[(3S,5R)-4-[2-(4-Cyano-phenyl)-acetyl]-3-(3,4-difluoro-phenyl)-5-methyl-2-oxo-[1,4]diazepan-1-yl]-3-naphthalen-1-yl-propionamide, 2-[3-(3-Chloro-phenyl)-4-[2-(4-cyano-phenyl)-acetyl]-5-methyl-2-oxo-[1,4]diazepan-1-yl]-3-naphthalen-1-yl-propionamide, e.g. (R)-2-[(3S,5R)-3-(3-Chloro-phenyl)-4-[2-(4-cyano-phenyl)-acetyl]-5-methyl-2-oxo-[1,4]diazepan-1-yl]-3-naphthalen-1-yl-propionamide, 2-[4-[2-(4-Amino-phenyl)-acetyl]-3-(3-chloro-phenyl)-5-methyl-2-oxo-[1,4]diazepan-1-yl]-3-naphthalen-1-yl-propionamide, e.g. (R)-2-[(3S,5R)-4-[2-(4-Amino-phenyl)-acetyl]-3-(3-chloro-phenyl)-5-methyl-2-oxo-[1,4]diazepan-1-yl]-3-naphthalen-1-yl-propionamide, 2-[4-[2-(4-Amino-phenyl)-acetyl]-5-methyl-2-oxo-3-(3-trifluoromethyl-phenyl)-[1,4]diazepan-1-yl]-3-naphthalen-1-yl-propionamide, e.g. (R)-2-[(3S,5R)-4-[2-(4-Amino-phenyl)-acetyl]-5-methyl-2-oxo-3-(3-trifluoromethyl-phenyl)-[1,4]diazepan-1-yl]-3-naphthalen-1-yl-propionamide, 2-[4-[2-(4-Dimethylamino-phenyl)-acetyl]-5-methyl-2-oxo-3-(3-trifluoromethyl-phenyl)-[1,4]diazepan-1-yl]-3-naphthalen-1-yl-propionamide, e.g. (R)-2-[(3S,5R)-4-[2-(4-Dimethylamino-phenyl)-acetyl]-5-methyl-2-oxo-3-(3-trifluoromethyl-phenyl)-[1,4]diazepan-1-yl]-3-naphthalen-1-yl-propionamide, 2-[4-[2-(3-Amino-phenyl)-acetyl]-3-(3-chloro-phenyl)-5-methyl-2-oxo-[1,4]diazepan-1-yl]-3-naphthalen-1-yl-propionamide, e.g. (R)-2-[(3S,5R)-4-[2-(3-Amino-phenyl)-acetyl]-3-(3-chloro-phenyl)-5-methyl-2-oxo-[1,4]diazepan-1-yl]-3-naphthalen-1-yl-propionamide, N-(4-{2-[4-(1-Carbamoyl-2-naphthalen-1-yl-ethyl)-7-methyl-3-oxo-2-(3-trifluoromethyl-phenyl)-[1,4]diazepan-1-yl]-2-oxo-ethyl)phenyl)-succinamic acid, e.g. N-(4-(2-[(2S,7R)-4-((R)-1-Carbamoyl-2-naphthalen-1-yl-ethyl)-7-methyl-3-oxo-2-(3-trifluoromethyl-phenyl)-[1,4]diazepan-1-yl]-2-oxo-ethyl}-phenyl)-succinamic acid, N-(4-{2-[4-(1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-succinamic acid, e.g. N-(4-{2-[(2S,7R)-4-((R)-1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-succinamic acid, N-(3-{2-[4-(1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-succinamic acid, e.g. N-(3-{2-[(2S,7R)-4-((R)-1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-succinamic acid, 2-[4 2-[4-(2-Amino-acetylamino)-phenyl]-acetyl]-3-(3-chloro-phenyl)-5-methyl-2-oxo-[1,4]diazepan-1-yl]-3-naphthalen-1-yl-propionamide, e.g. (R)-2-[(3S,5R)-4-{2-[4-(2-Amino-acetylamino)-phenyl]-acetyl}-3-(3-chloro-phenyl)-5-methyl-2-oxo-[1,4]diazepan-1-yl]-3-naphthalen-1-yl-propionamide, 2-[4-2-[3-(2-Amino-acetylamino)-phenyl]-acetyl]-3-(3-chloro-phenyl)-5-methyl-2-oxo-[1,4]diazepan-1-yl]-3-naphthalen-1-yl-propionamide, e.g. (R)-2-[(3S,5R)-4-(2-[3-(2-Amino-acetylamino)-phenyl]-acetyl}-3-(3-chloro-phenyl)-5-methyl-2-oxo-[1,4]diazepan-1-yl]-3-naphthalen-1-yl-propionamide, 2-[4-{2-[4-(3-Amino-propionylamino)-phenyl]-acetyl)-3-(3-chloro-phenyl)-5-methyl-2-oxo-[1,4]diazepan-1-yl]-3-naphthalen-1-yl-propionamide, e.g. (R)-2-[(3S,5R)-4-{2-[4-(3-Amino-propionylamino)-phenyl]-acetyl}-3-(3-chloro-phenyl)-5-methyl-2-oxo-[1,4]diazepan-1-yl]-3-naphthalen-1-yl-propionamide, N-(4-{2-[4-(1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-acrylamide, e.g. N-(4-(2-[4-((R)-1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-acrylamide, N-(4-{2-[4-(1-Carbamoyl-2-naphthalen-1-yl-ethyl)-2-(3-chloro-phenyl)-7-methyl-3-oxo-[1,4]diazepan-1-yl]-2-oxo-ethyl)phenyl)-4-morpholin-4-yl-4-oxo-butyramide, e.g. N-(4-{2-[(2S,7R)-4-((R)-1-Carbamoyl-2-naphthalen-1-yl-ethyl)-2-(3-chloro-phenyl)-7-methyl-3-oxo-[1,4]diazepan-1-yl]-2-oxo-ethyl)-phenyl)-4-morpholin-4-yl-4-oxo-butyramide, N-(4-2-[4-(1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-4-oxo-4-piperazin-1-yl-butyramide, e.g. N-(4-{2-[(2S,7R)-4-((R)-1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-4-oxo-4-piperazin-1-yl-butyramide, 2-{3-(3-Chloro-phenyl)-4-[2-(2-methoxy-phenyl)-acetyl]-5-methyl-2-oxo-[1,4]diazepan-1-yl}-3-naphthalen-1-yl-propionamide, e.g. (R)-2-(3S,5R)-3-(3-Chloro-phenyl)-4-[2-(2-methoxy-phenyl)-acetyl]-5-methyl-2-oxo-[1,4]diazepan-1-yl}-3-naphthalen-1-yl-propionamide, 2-{3-(3-Chloro-phenyl)-4-[2-(4-methoxy-phenyl)-acetyl]-5-methyl-2-oxo-[1,4]diazepan-1-yl}-3-naphthalen-1-yl-propionamide, e.g. (R)-2-{(3S,5R)-3-(3-Chloro-phenyl)-4-[2-(4-methoxy-phenyl)-acetyl]-5-methyl-2-oxo-[1,4]diazepan-1-yl}-3-naphthalen-1-yl-propionamide, 2-[4-[2-(3-Chloro-4-methoxy-phenyl)-acetyl]-(3-(3-chloro-phenyl)-5-methyl-2-oxo-1,4]diazepan-1-yl]-3-naphthalen-1-yl-propionamide, e.g. (R)-2-[(3S,5R)-4-[2-(3-Chloro-4-methoxy-phenyl)-acetyl]-(3-(3-chlorophenyl)-5-methyl-2-oxo-[1,4]diazepan-1-yl]-3-naphthalen-1-yl-propionamide, 2-[4-Acetyl-3-(3-chloro-phenyl)5-methyl-2-oxo-[1,4]diazepan-1-yl]-3-naphthalen-1-yl propionamide, e.g. (R)-2-[(3S,5R)-4-Acetyl-3-(3-chloro-phenyl)-5-methyl-2-oxo-[1,4]diazepam-1-yl]-3-naphthalen-1-yl propionamide, In another aspect the present invention provides a compound of formula I which is a compound of formula

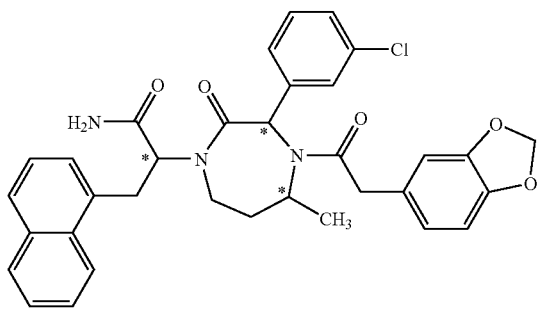

$I_{PREF}$ e.g. including the compound

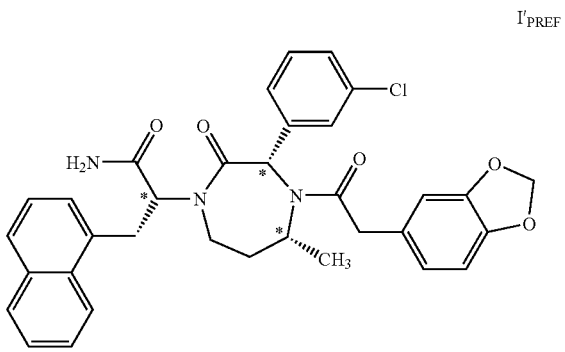

I'PREF

In another aspect the present invention provides (R)-2[(3S,5R)-4-(2-Benzo[1,3]dioxol-5-yl-acetyl)-3-(3-chloro-phenyl)-5-methyl-2-oxo-[1,4]diazepam-1-yl]-3-naphthalen-1-yl-propionamide.

If not otherwise defined herein
alkyl includes linear or branched $(C_{1-6})$alkyl, such as $(C_{1-4})$alkyl, e.g. $(C_{1-2})$alkyl, including unsubstituted or substituted alkyl, e.g. alkyl substituted by groups which are conventional in organic chemistry, e.g. halogen, OH, $NH_2$ or halo$(C_{1-6})$alky, haloalkyl includes halo$(C_{1-6})$alkyl, such as halo$(C_{1-4})$alkyl, e.g. halo$(C_{1-2})$alkyl, wherein one or more halogen(s) is (are) present in the alkyl group, preferably —$CF_3$, halogen includes fluoro, chloro, bromo, iodo, e.g. fluoro, chloro, bromo, preferably fluoro or chloro, amino includes unsubstituted and substituted amino, e.g. amino substituted by $(C_{1-4})$alkylamino, di$(C_{1-4})$alkylamino and amino substituted by acyl, acyl includes acyl, having 1 to 12 carbon atoms altogether, e.g. carboxy$(C_{1-4})$alkylcarbonyl, such as carboxy$(C_{1-3})$alkylcarbonyl, amino$(C_{1-4})$alkylcarbonyl, such as amino-$(C_{1-3})$alkylcarbonyl, $(C_{2-4})$alkenylcarbonyl or heterocyclylcarbonyl$(C_{1-4})$alkylcarbonyl, wherein heterocyclyl has 5 or 6 ring members and 1 to 4 heteroatoms, preferably 1 or 2 heteroatoms, selected from N, O, S, preferably N, O e.g. piperazinyl or morpholinyl, heterocyclyl includes heterocyclyl having 5 or 6 ring members and 1 to 4 heteroatoms selected from N, O, S, preferably N, O such as alicyclic and aromatic heterocyclyl, e.g. heterocyclyl having 6 ring members and 1 to 2 heteroatoms selected from N, O e.g. piperazinyl, morpholinyl, pyrimidinyl, aryl includes $(C_{6-18})$aryl, e.g. phenyl, and $(C_{6-18})$aryl, e.g. phenyl, annelated with heterocyclyl having 5 or 6 ring members and 1 to 4 heteroatoms selected from N, O, S, preferably N, O e.g. heterocyclyl having 5 ring members and 2 heteroatoms selected from N, O preferably benzo(1,3)dioxol-4-yl, benzo(1,3)dioxol-5-yl, quinolin-5-yl, quinolin-6-yl, quinolin-7-yl, quinolin-8-yl.

Compounds provided by the present invention, e.g. including compounds of formula I, $I_A$, $I_{PREF}$ and $I'_{PREF}$ are hereinafter designated as "compound(s) of (according to) the present invention". Each single substituent defined above in a compound of the present invention may be per se a preferred substituent, independently of the other substituents defined.

A compound of the present invention includes a compound in any form, e.g. in free form, in the form of a salt, in the form of a solvate and in the form of a salt and in the form of a solvate. A compound of the present invention in free form may be converted into a corresponding compound in the form of a salt; and vice versa. A compound of the present invention in free form or in the form of a salt and in the form of a solvate may be converted into a corresponding compound in free form or in the form of a salt in unsolvated form; and vice versa.

In another aspect the present invention provides a compound of the present invention in the form of a salt.

A salt of a compound of the present invention includes a pharmaceutically acceptable salt, e.g. including a metal salt or an acid addition salt. Metal salts include for example alkali or earth alkali; acid addition salts include salts of a compound of formula I with an acid, e.g. acetic acid, trifluoroacetic acid, hydrochloric acid.

A compound of the present invention may exist in the form of isomers and mixtures thereof; e.g. optical isomers, diastereoisomers, cis/trans isomers. A compound of the present invention may e.g. contain asymmetric carbon atoms and may thus exist in the form of diastereoisomeres and mixtures thereof or enantiomers or mixtures thereof, e.g. racemates. For example the groups $R_1$, $R_3$ and the group naphthylmethyl in position * in a compound of formula I may be in the (R)- or in the (S)-configuration, e.g. including mixtures therof. Preferably the naphthylmethyl group and $R_1$ in a compound of formula I both are in the (R)-configuration and $R_3$ is in the (S)-configuration. Isomeric mixtures may be separated as appropriate, e.g. according, such as analogously, to a method as conventional, to obtain pure isomers. The present invention includes a compound of the present invention in any isomeric form and in any isomeric mixture.

Similar considerations apply in relation to starting materials exhibiting isomeric features, e.g. analogously as indicated above.

Any compound described herein, e.g. a compound of the present invention, may be prepared as appropriate, e.g. according, e.g. analogously, to a method as conventional, e.g. or as specified herein. Starting materials are known or may be prepared according, e.g. analogously, to a method as conventional or as described herein.

In another aspect the present invention provides a process for the preparation of a compound of the present invention comprising A) reacting a compound of formula

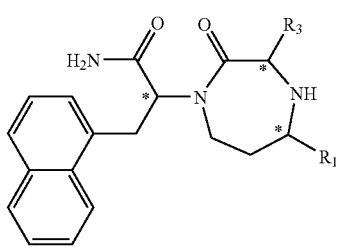

II wherein $R_1$ and $R_3$ are as defined above, with a compound of formula

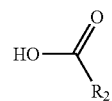

III e.g. in a protected form, e.g. in the presence of a
condensing agent, e.g. a carbodiimide
a base, e.g. an amine, such as diidopropylethylamine or dimethylaminopyridine, in organic solvent, e.g. polar organic solvent, such as N,N-dimethylformamide, optionally deprotecting, and optionally further reacting, to obtain a compound of formula I and isolating a compound of formula I,

OR

B) reacting a compound of formula

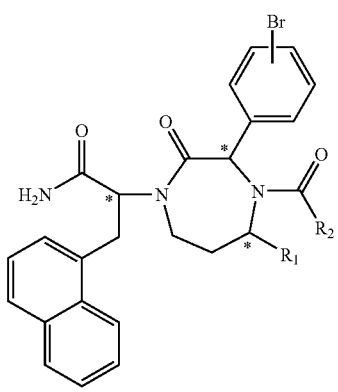

IV wherein $R_1$ and $R_2$ are as defined above, with an optionally substituted compound of formula

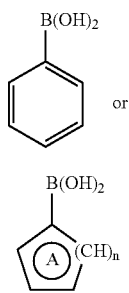

$V_A$ or $V_B$ wherein A denotes an aromatic heterocyclyl having 5 (n=1) or 6 (n=2) ring members and 1 to 4 heteroatoms selected from N, O, S, e.g. in the presence of a catalyst, e.g. $Pd(PPh_3)_4$, to obtain a compound of formula I wherein $R_3$ is phenyl substituted by optionally substituted phenyl or aromatic heterocyclyl having 5 or 6 ring members and 1 to 4 heteroatoms selected from N, O, S, and isolating a compound of formula I obtained from the reaction mixture.

An optionally protected group $R_2$ of formula III e.g. includes phenyl substituted by an amine. Such amine may be protected by an appropriate protection group, e.g. including tert-butoxycarbonyl (Boc), which protecting group may be removed after reaction of a compound of formula III with a compound of formula II to obtain a free amine group. Further reacting e.g. includes alkylating or acylating such amine group as appropriate, e.g. according, e.g. analogously, to a method as conventional.

In an intermediate of formula II or of formula IV (starting materials), functional groups, if present, optionally may be in protected form or in the form of a salt, if a salt-forming group is present. Protecting groups, optionally present, may be removed at an appropriate stage, e.g. according, e.g. analogously, to a method as conventional A compound of formula I thus obtained may be converted into another compound of formula I, e.g. or a compound of formula I obtained in free form may be converted into a salt of a compound of formula I and vice versa.

In another aspect the present invention provides
a compound of formula II wherein $R_1$ and $R_3$ are as defined above, and
a compound of formula IV, wherein $R_1$ and $R_2$ are defined as above, e.g. useful as intermediates for the production of a compound of the present invention.

The above reaction A) is a an amine acylation reaction and may be carried out as appropriate, e.g. according, e.g. analogously, to a method as conventional or as described herein. The above reaction B) is a cross coupling reaction and may be carried out as appropriate, e.g. according, e.g. analogously, to a method as conventional or as described herein.

Any compound described herein, e.g. a compound of the present invention and intermediates of formula II and IV, may be prepared as appropriate, e.g. according, e.g. analogously, to a method as conventional, e.g. or as specified herein.

The compounds of the present invention exhibit valuable pharmacological properties, e.g. by mediating, such as inhibiting, the activity of LFA-1/ICAM-1, LFA-1/ICAM-2, LFA-1/ICAM-3 or LFA-1/JAM-1 interactions and thus mediating, e.g. inhibiting inflammation, e.g. as indicated in in vitro and in vivo TEST SYSTEMS herein and are therefore indicated for therapy.

A. In Vitro Test System: (Cell Free Assay)

The assay determines the binding of soluble human ICAM-1 to immobilized human LFA-1. LFA-1 is purified from JY cells, a human lymphoblastoid B cell-line, by immunoaffinity chromatography analogously as described by Dustin et al., J. Immunol. 148, 2654-2663, 1992. ICAM-1 mouse Cκ fusion protein (ICAM-1) is produced using the baculovirus system as described by Weitz-Schmidt et al., Anal. Biochem. 238, 184-190, 1996.

Purified LFA-1 is diluted 1:20 in phosphate buffered saline (PBS) containing 2 mM $MgCl_2$, pH 7.4 and coated onto microtiter plates (Nunc) at 37° for 3 hours. Plates are blocked with 1% heat-treated bovine serum albumin in PBS for 2 hours at 37° followed by a washing step using PBS, 2 mM $MgCl_2$, 1% fetal calf serum, pH 7.4 (assay buffer). Compounds of the present invention (10 mM solution in DMSO) are diluted in assay buffer and added to the plates. Biotinylated recombinant ICAM-1 in assay buffer (6 μg/ml) is added and allowed to bind at 37° for one hour. After incubation, wells are washed with assay buffer. Streptavidin-peroxidase diluted 1:5000 in assay buffer is added and incubated for 45 min at 37°. Plates are washed with assay buffer and 2,2'-azino-bis(3-ethylbenzothiazoline-6-sulfonic acid) diammonium salt substrate solution is added to each well. The reaction is stopped after 20 minutes and bound ICAM-1 is determined by measuring the optical density at 405 nm in a microplate reader.

In this assay the compounds of the present invention exhibit activity, e.g. the compounds of the present invention inhibit adhesion of LFA-1 to ICAM-1 with an $IC_{50} \leq 50$ μM, preferably 0.05 to 50 μM. The compounds of examples 13 and 14 are preferred compounds of the present invention and show $IC_{50}$ values of 0.43 or 0.09 μM, respectively, in this assay. We have surprisingly found that compounds of formula I, wherein $R_3$ is substituted phenyl show higher $IC_{50}$ values in such LFA-1 in vitro TEST SYSTEM than compounds of formula I, wherein $R_3$ is unsubstituted phenyl.

B. In Vivo Test System: Allergic Contact Dermatitis (ACD)

Groups of 8 female NMRI mice are sensitized on the shaved abdomen with 50 μl of oxazolone (2% in acetone) and challenged with 10 μl of 0.2% oxazolone on the inner surface of the right ear 7 days later. The unchallenged left ears serve as normal controls and dermatitis is evaluated from the individual differences in auricular weights, which are taken as a measure of inflammatory swelling 24 hours after the challenge. Dermatitis is evaluated in test- and control groups. The test groups are treated with the test compounds orally (2 hours after challenge), the controls are treated similarly with the vehicles alone. For oral administration the compounds are administered in an oil in $H_2O$ emulsion. The data of the test- and the vehicle-treated control groups are statistically analysed by ANOVA followed by Dunnet T-test (normal distribution or data) or by H and U-test, respectively. When administered p.o. at a dose of from 0.03 to 30 mg/kg, the compounds of the present invention inhibit the elicitation phase of allergic contact dermatitis. For example, compound of Example 14 has an inhibiting effect in this assay of >30% when administered p.o. at a dose of 0.03 mg/kg.

The compounds of the present invention are therefore expected to be useful in the treatment of diseases or disorders mediated by interactions of LFA-1 with its ligands involved in cell adhesion, migration and activation. The compounds may be preferably useful for treatment of inflammatory conditions, allergic diseases or autoimmune diseases. Examples are inflammatory injuries of the skin (psoriasis, eczemas, urticaria, acne, pyoderma gangrenosum, sun burns or toxic epidermal necrolysis), lung (adult respiratory distress syndrome, COPD), kidney (acute/chronic interstitial/glomerulonephritis), liver (acute/chronic hepatitis, granulomatous diseases), cardiovascular system (ischemia/reperfusion injuries, shock, arteriosclerosis, vasculitides), eye (conjunctivitis, keratitis) or gastrointestinal tract (Crohn's disease, ulcerative colitis). Examples of allergic conditions are allergic contact dermatitis, atopic dermatitis or asthma. Rheumatoid arthritis, multiple sclerosis, (systemic) lupus erythematosus, Sjogren' syndrome, alopecia areata, uveitis, lichen planus, pemphigus, bullous pemphigoid, epidermolysis bullosa or myasthenia gravis are examples of auto-immune mediated conditions.

The compound of the present invention may also be used for prevention of acute and chronic rejection of allo- or xenografts, transplantation, host vs. graft or graft vs. host diseases, for the treatment of neoplastic diseases including metastasis of neoplastic or cancerous growth or cancer, AIDS and infectious diseases.

Treatment includes prophylaxis.

The compound of the present invention may be preferably useful for treatment of psoriasis, rheumatoid arthritis, inflammatory bowel diseases (Crohn's disease, ulcerative colitis), (systemic) lupus erythematosus, atopic dermatitris, Sjogren' syndrom, rejection after transplantation and graft vs. host disease.

In one preferred aspect the compounds of the present invention are useful in the treatment of autoimmune diseases, e.g. rheumatoid arthritis, or of inflammatory diseases, e.g. psoriasis or atopic dermatitis, such as rheumatoid arthritis.

For the above uses the required dosage will of course vary depending on the mode of administration, the particular condition to be treated and the effect desired. In general, satisfactory results are indicated to be obtained systemically at daily dosages of a compound of the present invention from about 0.1 mg/kg to about 100 mg/kg body weight. An indicated daily dosage in the larger mammals, e.g. humans, is in the range from about 0.5 mg to about 500 mg (e.g. about 0.00625 mg/kg to about 6.25 mg/kg), conveniently administered, for example, in divided doses up to four times a day or in retard form.

The compounds of the present invention may be administered systemically or topically, by any conventional route, in particular enterally, e.g. orally, e.g. in the form of tablets or capsules, topically, e.g. in the form of lotions, gels, ointments or creams, or in a nasal or a suppository form. Percutaneous administration via patches or other delivery systems may also be a possible route for prophylaxis or treatment of above diseases.

For topical use, e.g. including administration to the eye, satisfactory results may be obtained with local administration of a 0.5-10%, such as 1-3% concentration of active substance several times daily, e.g. 2 to 5 times daily.

In another aspect the present invention provides a compound of the present invention for use as a pharmaceutical, e.g. against diseases as indicated above, such as rheumatoid arthritis.

For pharmaceutical use a compound of the present invention includes one or more, preferably one, compounds of the present invention, e.g. a combination of two or more compounds of the present invention.

In another aspect the present invention provides the use of a compound of the present invention for the manufacture of a medicament, e.g. a pharmaceutical composition, for the treatment of a disease as indicated above, for example of diseases mediated by LFA-1/ICAM-1, LFA-1/ICAM-2, LFA-1/ICAM-3 or LFA-1/JAM-1 interactions, e.g against inflammatory diseases, allergic conditions or autoimmune diseases, such as autoimmune diseases, e.g. psoriasis, asthma or rheumatoid arthritis.

In another aspect the present invention provides a pharmaceutical composition comprising a compound of the present invention in association with at least one pharmaceutically acceptable excipient, e.g. including a carrier and/or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers.

Such compositions may be manufactured according, e.g. analogously, to a method as conventional, e.g. by mixing a compound of the present invention with a pharmaceutically acceptable excipient, e.g. a carrier and/or diluent. Unit dosage forms for oral administration contain, for example, from about 0.1 mg to about 1000 mg (e.g. from about 0.00125 mg/kg to about 12.5 mg/kg), e.g. 0.5 mg to 500 mg, such as e.g. 1 mg to about 125 mg of a compound of the present invention.

The compounds of the present invention may be administered in the form of a pharmaceutically acceptable salt, e.g. an acid addition salt or metal salt; or in free form; optionally in the form of a solvate. The compounds of the present invention in the form of a salt exhibit the same order of activity as the compounds of the present invention in free form; optionally in the form of a solvate.

In another aspect the present invention provides:

A method for treatment of disorders or diseases mediated by LFA-1/ICAM-1, LFA-1/ICAM-2, LFA-1/ICAM-3 or LFA-1/JAM-1 interactions, e.g. such as indicated above, in a subject in need of such treatment, which method comprises administering to said subject an effective amount of a compound of the present invention; and A method for treatment of diseases as indicated above, e.g. inflammatory, allergic or autoimmune diseases, e.g. as indicated above, e.g. psoriasis, asthma, rheumatoid arthritis, in a subject in need of such treatment, which method comprises administering to said subject an effective amount of a compound of the present invention.

For such treatment, the appropriate dosage will, of course, vary depending upon, for example, the chemical nature and the pharmakokinetic data of a compound of the present invention employed, the individual host, the mode of administration and the nature and severity of the conditions being treated. However, in general, for satisfactory results in larger mammals, for example humans, an indicated daily dosage is in the range from about 0.01 g to about 1.0 g (e.g. from about 0.125 mg/kg to about 12.5 mg/kg), of a compound of the present invention; conveniently administered, for example, in divided doses up to four times a day.

A compound of the present invention may be administered by any conventional route, for example enterally, e.g. including nasal, buccal, rectal, oral, administration; parenterally, e.g. including intravenous, intramuscular, subcutanous administration; or topically; e.g. including epicutaneous, intranasal, intratracheal administration;

e.g. in form of coated or uncoated tablets, capsules, injectable solutions or suspensions, e.g. in the form of ampoules, vials, in the form of creams, gels, pastes, inhaler powder, foams, tinctures, lip sticks, drops, sprays, or in the form of suppositories.

A compound of the present invention may be used for pharmaceutical treatment according to the present invention alone or in combination with at least one, e.g. one or more, other pharmaceutically active agents. Such other pharmaceutically active agents e.g. include compounds active in immunomodulating regimens or other anti-inflammatory agents, e.g. for the treatment or prevention of inflammatory or allergic conditions, autoimmune disorders, or acute or chronic rejection of allo- or xenograft. For example, compounds of the present invention may be used in combination with cyclosporins, rapamycins or ascomycins, or their immunosuppressive analogs, e.g. cyclosporin A, cyclosporin G, FK-506, ASM 981, rapamycin, 40-O-(2-hydroxy)ethyl-rapamycin etc., corticosteroids, cyclophosphamide, azathioprene, methotrexate, FTY 720, leflunomide, mizoribine, mycophenolic acid, mycophenolate mofetil, 15-deoxyspergualine, immunosuppressive monoclonal antibodies, e.g., monoclonal antibodies to leukocyte receptors, e.g., MHC, CD2, CD3, CD4, CD7, CD25, CD28, B7, CD40, CD45, or CD58 or their ligands, or other immunomodulatory compounds, e.g. CTLA4Ig, or other adhesion molecule inhibitors, e.g. mAbs or low molecular weight inhibitors including selectin antagonists and VLA-4 antagonists.

Combinations include fixed combinations, in which two or more pharmaceutically active agents are in the same formulation; kits, in which two or more pharmaceutically active agents in separate formulations are sold in the same package, e.g. with instructions for co-administration; and free combinations in which the pharmaceutically active agents are packaged separately, but instructions for simultaneous or sequential administration are given.

If the compounds of the present invention are administered in combination with other immunosuppressive/immunomodulatory or anti-inflammatory active agents, e.g. for preventing or treating acute or chronic rejection or inflammatory or autoimmune disorders as hereinabove specified, dosages of the co-administered immunosuppressant, immunomodulatory or anti-inflammatory compound will of course vary depending on the type of co-drug employed, e.g. whether it is a steroid or a cyclosporin, on the specific drug employed, on the condition being treated and so forth. In general comparable dosage ranges as indicated for the co-administration may be are appropriate.

In another aspect the present invention provides a pharmaceutical composition according to the present invention, further comprising another pharmaceutically active agent.

In another aspect the present invention provides

A method for treatment of disorders or diseases as indicated above comprising co-administrating, e.g. concomitantly or in sequence, a therapeutically effective amount of at least one compound of the present invention and at least one second pharmaceutically active agent, said pharmaceutically active agent being selected from the group consisting of immunosuppressants, immunomodulatory or anti-inflammatory active agents, e.g. such as indicated above; and A pharmaceutical combination, e.g. a kit, for use in a method for treatment according to the present invention, comprising at least one compound of the present invention to be used concomitantly or in sequence with at least one immunosuppressant, immunomodulatory or anti-inflammatory active agent. The kit may comprise instructions for concomitant administration or administration in sequence.

In another aspect the present invention provides a compound of formula

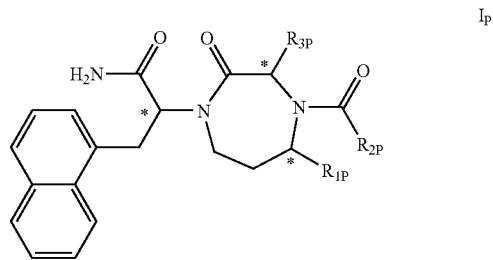

wherein
$R_{1P}$ is $(C_{1-4})$alkyl,
$R_{2P}$ is $(C_{1-4})$alkyl or —$(CH_2)_n$-$R_{4P}$, wherein
  n is 1, 2, 3 or 4 and
  $R_{4P}$ is unsubstituted or substituted
    phenyl or
    phenyl annelated with another ring system, which other ring system is a 5- or 6-membered heterocycle, having one to 4 heteroatoms selected from N, O, S, e.g. wherein substituents are selected from the group consisting of
    halogen,
    unsubstituted amino or amino substituted by one or two $(C_{1-4})$alkyl,
    cyano,
    $(C_{1-4})$alkoxy,
    $(C_{1-6})$haloalkyl and
$R_{3P}$ is substituted phenyl, e.g. one or morefold, wherein the substituents are selected from the group consisting of
  halogen,
  $(C_{1-6})$haloalkyl, unsubstituted or substituted phenyl, wherein substitutents are as indicated under "substituted phenyls" in the meaning of $R_{4P}$, e.g. in the form of a salt and/or solvate.

In the following examples all temperatures are in degree (°) Celsius. In the reaction schemes and corresponding description $R_2$ and $R_3$ are as defined above.

The following ABBREVIATIONS are used:

| AcOH | acetic acid | Boc | tert.-butoxy-carbonyl |
|---|---|---|---|
| DBU | 1,4-diaza-bicyclo[5.4.0]undec-7-en | DIEA | diisopropylethylamine |
|  |  | DMAP | N,N-dimethyl-4-aminopyridine |
| DIPCI | diisopropylcarbodiimide |  |  |
| DMF | N,N-dimethylformamide | EtAc | ethyl acetate |
| equiv. | equivalent | EX | example |
| HOAt | 1-hydroxy-7-azabenzo-triazole | i-PrOH | isopropanol |
|  |  | NMM | N-methyl-morpholine |
| MeOH | methanol | THF | tetrahydrofurane |
| rt | room temperature | TsOH | p-toluenesulfonic acid |
| TFA | trifluoroacetic acid |  |  |
| Z | benzyloxycarbonyl |  |  |
| EDC | N-ethyl-N'-(3-dimethyl-aminopropyl)-carbodiimide |  |  |
| EDC-HCl | N-ethyl-N'-(3-dimethyl-aminopropyl)-carbodiimide in the form of a hydrochloride |  |  |

EXAMPLES

Procedure A

Synthesis of Compounds of the Present Invention

Aa. Synthesis of a Ketal Intermediate

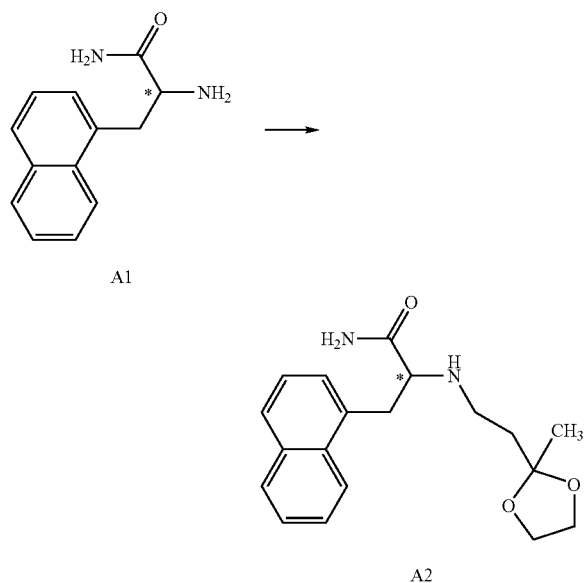

Naphthylalanine amide of formula A1 and 0.3 equiv. of NMM are dissolved in dioxane and 1.5 equiv. of methylvinylketone are added. The mixture obtained is stirred at RT for 15 hours and 5 equiv. of 2-methoxydioxolane and 1.5 equiv. of TsOH-monohydrate are added. The mixture obtained is stirred and diluted with EtAc. The organic phase obtained is washed and dried, solvent is evaporated and a ketal intermediate of formula A2 is obtained, which is optionally purified or used without further purification.

Ab. Amine-Protection of Phenylglycines

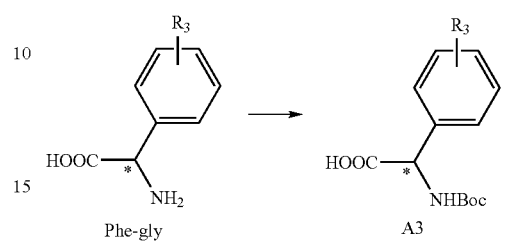

A compound of formula Phe-gly, wherein $R_3$ is as defined above, is dissolved in MeOH. 2 equiv. of $NaHCO_3$ and 1.2 equiv. of Boc-anhydride are added to the solution obtained and the suspension obtained is heated at 50° under stirring. From the mixture obtained solvent is evaporated and $H_2O$ and toluene are added. The phases obtained are separated and the organic phase obtained is extracted with 1N NaOH. The pH of the aqueous phase obtained is adjusted to pH 3 and the mixture obtained is extracted with EtAc. The organic phase obtained is dried, solvent is evaporated and racemic Boc-phenylglycine of formula A3, wherein $R_3$ is as defined above, is obtained.

Ac. Amine Acylation

Compound of formula A2 ⟶

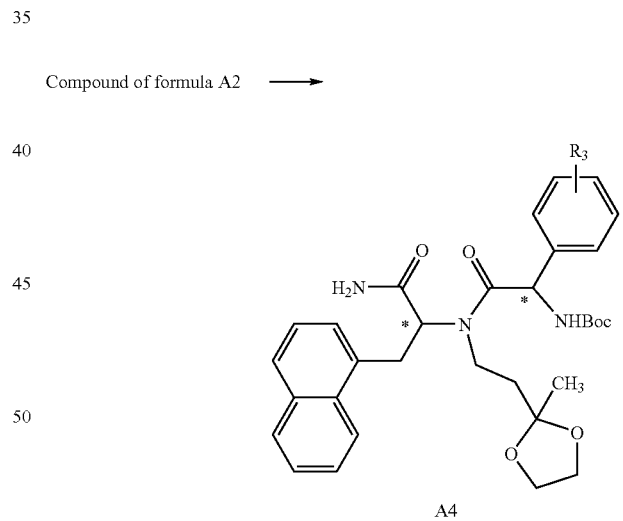

1 equiv. of a compound of formula A2, wherein $R_3$ is as defined above, 1.5 equiv. of racemic (substituted) Boc-phenylglycine of formula A3, wherein $R_3$ has the meaning as indicated above, and 0.12 equiv. of HOAt are dissolved in DMF. 1.5 equiv. of DIEA and 1.5 equiv. of EDC in free base form are added during 15 hours at rt. Solvent is evaporated, the evaporation residue obtained is diluted with EtAc and extracted with 1N HCl and 5% $NaHCO_3$ solution. The organic phase obtained is dried and solvent is evaporated. A compound of formula A4, wherein $R_3$ is as defined above, is obtained in the form of a diastereoisomeric mixture.

Ab. Deprotection and Reductive Ring Closure

Compound of formula A4 →

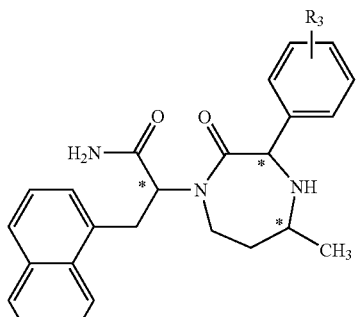

A5

A compound of formula A4, wherein $R_3$ is as defined above, is dissolved in TFA/H$_2$O at 0°. The mixture obtained is stirred, quenched with H$_2$O and solvent is evaporated. A diastereoisomeric mixture of a compound of formula A4, wherein the Boc-NH— group is deprotected is obtained and is dissolved in MeOH/H$_2$O. The pH of the mixture obtained is adjusted to pH 5. 0.5 equiv. of a NaCNBH$_3$-solution in MeOH/H$_2$O are added at 0° to the mixture obtained, the mixture obtained is stirred, solvent is evaporated and the evaporation residue obtained is diluted with EtAc. 3.5 M phosphate-buffer of pH 4 are added to the mixture obtained, two phases are obtained and are separated. The organic phase obtained is extracted with 5% NaHCO$_3$ solution, dried and solvent is evaporated. A compound of formula A5, wherein $R_3$ is as defined above, is obtained.

Ae. Acylation of Diazepanes

Compound of formula A5 →

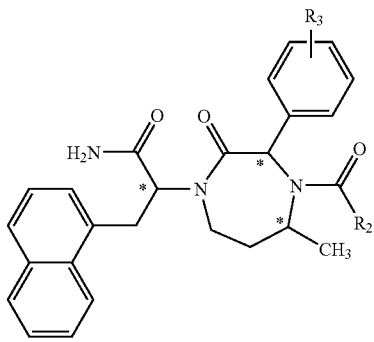

A6

A compound of formula A5, wherein $R_3$ is as defined above, is treated with 1.7 equiv. of R$_2$COOH, wherein R$_2$ is as defined above, 1.3 equiv. of DIEA and 0.2 equiv. of HOAt in DMF. The mixture obtained is heated to 35° and 1.7 equiv. of EDC are added and the mixture obtained is stirred for 15 hours at 35°. From the mixture obtained solvent is evaporated, the evaporation residue obtained is dissolved in EtAc and extracted with 1N HCl and 5% NaHCO$_3$ solution. The organic phase obtained is dried and solvent is evaporated. A compound of formula A6 is obtained, which is optionally subjected to chromatography (e.g. silica gel, toluene/i-PrOH), in order for further purification, if desired.

Procedure B

The compound of example 22 is treated with 1.5 equiv. of N-Boc-beta-alanine, or N-Boc-glycine, respectively, 1.5 equiv. of EDC-HCl and 0.5 equiv. of DMAP in DMF at rt. The mixture obtained is diluted with EtAc and 1N HCl, two phases are obtained and are separated, the organic phase obtained is washed, dried and solvent is evaporated. The evaporation residue obtained is dissolved in TFA/H$_2$O at 0°, stirred, diluted with dioxane and solvent is evaporated. A residue obtained is subjected to RP-chromatography. The compounds of example 31 and example 29, respectively, in the form of a trifluoroacetate are obtained. When using the compound of example 25 and N-Boc-glycine, the compound of example 30 is obtained.

Procedure C

The compound of example 31 is treated with an excess of CH$_3$J in CH$_2$Cl$_2$/K$_2$CO$_3$ at rt. From the mixture obtained solvent is evaporated, the evaporation residue obtained is dissolved in MeOH/H$_2$O and worked up by solid-phase extraction (C-18 cartridge, MeOH/H$_2$O gradient). The compound of example 32 is obtained.

Procedure D

The compound of example 22, or example 23, respectively, is treated with succinic acid anhydride. Depending on the starting materials, the compound of example 27, or example 27, respectively, is obtained.

Procedure E

The compound of example 27 is treated with 6 equiv. of morpholine and 2 equiv. of EDC-HCl in DMF at 0° for 4 hours at pH 8 (adjustment by addition of TFA). The mixture obtained is diluted with EtAc and 1N HCl, two phases obtained are separated, the organic phase obtained is washed, dried and solvent is evaporated. The compound of example 33 is obtained.

Procedure F

The compound of example 27 is treated with 6 equiv. of piperazine and 2 equiv. of EDC-HCl in DMF at pH=8 (pH-adjustment by addition of TFA). The mixture obtained is diluted with EtAc and 5M pH 4 phosphate buffer, two phases obtained are separated, the organic phase obtained is washed, dried and solvent is evaporated. The compound of example 34 is obtained.

Procedure G

The compound of example 5 is treated with phenylboronic acid, or pyrimidine-5-boronic acid, respectively, in the presence of a catalytic amount of palladium tetrakistriphenylphosphine in dimethoxyethane/aqeous Na$_2$CO$_3$-solution (6:1) at 130° for 10 minutes in a closed vessel. The mixture obtained is diluted with EtAc, extracted at pH 4 with phosphate buffer and aqueous Na$_2$CO$_3$ solution, and, from the organic layer obtained, solvent is evaporated. Depending on the boronic acid used, a compound of example 6, or 12b, respectively, is obtained. A compound of example 6 is treated with trifluoroacetic acid and the compound of example 6 is obtained in the form of a trifluoroacetate.

Analogously to procedures as described above, but using appropriate starting materials, compounds of formula I wherein R$_1$ is methyl and R$_2$ and R$_3$ are as defined in TABLE 1 below are obtained.

The compounds of examples
1-5, 7-25, 27-28 and 35-38 are prepared according to procedure A;
6 and 12b are prepared according to procedure G;
26 and 27 are prepared according to procedure D;
29-31 are prepared according to procedure B;
32 is prepared according to procedure C;
33 is prepared according to procedure E;
34 is prepared according to procedure F The compounds of examples 6, 11, 23, 25, 29 and 31 are obtained in the form of a trifluoroacetate.

Under "DATA" in TABLE 1 there are also indicated $R_f$ values (thin layer chromatography on silica gel 60, in toluene/i-PrOH 1:1 (=T) or EtAc (=E);

$^1$H-NMR data in CDCl$_3$, unless otherwise indicated.

TABLE 1

| EX | R$_2$ | R$_3$ | DATA |
|---|---|---|---|
| 1 | 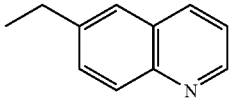 | 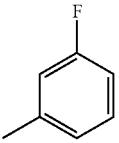 | $R_f$=0.55(T). δ=8.84(dd, 4Hz, 1Hz), 8.82(dd), 8.11(d, 9Hz), 8.07(d, 8Hz), 8.00(d, 9Hz), 7.97(d, 9Hz), 7.90(d, 8Hz), 7.83(d, 8Hz), 7.76(d, 8Hz), 7.54(m), 7.29(m), 7.20(dd, 8Hz, 4Hz), 7.06(d, 8Hz), 6.99(d, 9Hz), 6.59(d, 8Hz), 6.54(s), 6.38(s br, NH), 6.29(s br, NH), 6.05(s), 5.62(dd, 8Hz, 8Hz), 5.48(dd, 7Hz, 7Hz), 5.38(s br, NH), 4.62(m), 4.00(d, 15Hz), 3.88(d, 15Hz), 2.78(dd, 13Hz, 12Hz), 0.62(d, 7Hz), 0.59(d, 7Hz) |
| 2 | 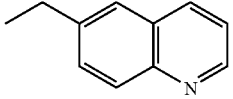 | 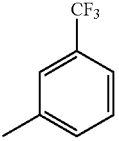 | $R_f$=0.37(T); δ=8.81(dd, 4Hz, 1Hz), 8.01(d, 9Hz), 7.99(d, 9Hz), 7.91(d, 8Hz), 7.04(d, 8Hz), 6.83(s), 6.02(s), 5.70(dd, 9Hz, 7Hz), 5.49(dd, 7Hz, 7Hz), 4.60(m), 4.02(d, 15Hz), 3.93(d, 15Hz), 2.87(dd, 13Hz, 11Hz), 0.57(d, 7Hz), 0.50(d, 7Hz) |
| 3 | 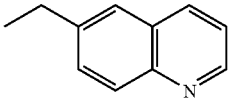 | 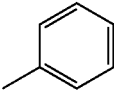 | $R_f$=0.65(T). δ=8.84(dd, 4Hz, 2Hz), 8.11(d, 9Hz), 8.07(d, 8Hz), 8.00(d, 9Hz), 7.97(d, 9Hz), 7.90(d, 7Hz), 7.83(d, 8Hz), 7.76(d, 8Hz), 7.64(m), 7.55(m), 7.41(m), 7.00(dd, 9Hz, 9Hz), 6.79(m), 6.54(s br), 6.30(s br), 6.04(s), 5.63(dd, 8Hz, 8Hz), 5.49(dd, 7Hz, 7Hz), 5.40(s br), 4.61(m), 3.99(d, 15Hz), 3.87(d, 15Hz), 2.78(dd, 13Hz, 11Hz), 0.59(d, 7Hz), 0.54(d, 7Hz) |
| 4 | 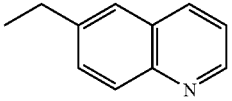 | 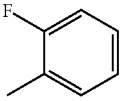 | $R_f$=060(T). δ=8.83(dd, 4Hz, 1Hz), 8.74(dd, 4Hz, 1Hz), 8.11(d, 9Hz), 8.02(d, 9Hz), 7.96(d, 9Hz), 7.89(d, 8Hz), 7.81(d, 8Hz), 7.75(d, 8Hz), 6.56(s br), 6.21(s), 5.55(dd, 8Hz, 8Hz), 5.52(dd, 7Hz, 7Hz), 5.42(s br), 5.38(s br), 4.62(m), 3.95(d, 15Hz), 3.83(d, 15Hz), 3.55(dd, 16Hz, 7Hz), 3.45(dd, 15Hz, 8Hz), 3.30(dd, 13Hz, 11Hz), 3.19(dd, 15Hz, 8Hz), 2.81(dd, 13Hz, 12Hz), 1.84(ddd, 15Hz, 7Hz, 7Hz), 0.56(d, 7Hz), 0.54(d, 7Hz) |
| 5 | 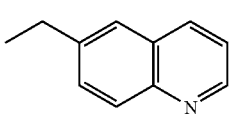 | 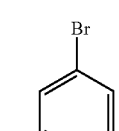 | $R_f$=0.32(T). δ=8.84(dd, 4Hz, 2Hz), 8.15(d, 8Hz), 8.10(d, 8Hz), 8.01(d, 8Hz), 8.00(d, 8Hz), 7.91(d, 8Hz), 7.85(d, 8Hz), 7.77(d, 8Hz), 7.69(s), 7.66(s), 7.63(dd, 7Hz, 8Hz), 7.55(dd, 8Hz, 8Hz), 7.42(m), 7.35(dd, 4Hz, 8Hz), 7.29(d, 8Hz), 7.19(d, 7Hz), 6.99(dd, 8Hz, 8Hz), 6.78(s), 6.74(d, 8Hz), 6.54(s br), 6.30(s br), 6.01(s), 5.63(dd, 8Hz, 8Hz), 5.48(dd, 7Hz, 7Hz), 5.43(s br), 5.35(s br), 4.62(m), 4.01(d, 15Hz), 3.92(m), 3.89(d, 16Hz), 3.69(dd, 15Hz, 8Hz), 3.65(d, 16Hz), 3.54(dd, 15Hz, 8Hz), 3.42(dd, 15Hz, 8Hz), 3.41(dd, 15Hz, 9Hz), 3.34(dd, 12Hz, 11Hz), 2.78(dd, 13Hz, 11Hz), 1.86(ddd, 15Hz, 6Hz, 6Hz), 0.63(d, 7Hz), 0.58(d, 7Hz) |

TABLE 1-continued

| EX | R₂ | R₃ | DATA |
|---|---|---|---|
| 6 | 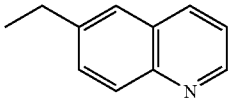 | 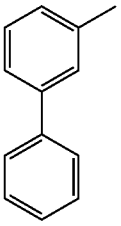 | R_f=0.34(T 4:1). δ=9.15(dd, 5Hz, 1Hz), 9.09(dd, 5Hz, 1Hz), 8.66(d, 8Hz), 8.47(d, 9Hz), 8.42(d, 9Hz), 8.42(d, 8Hz), 8.02(d, 8Hz), 7.98(d, 9Hz), 7.97(s), 7.93(d, 7Hz), 7.91(s), 7.67(dd, 12Hz, 1Hz), 7.65(dd, 13Hz, 1Hz), 7.60(m), 7.50(ddd, 8Hz, 8Hz, 3Hz), 6.99(d, 7Hz), 6.94(s), 6.91(s br), 6.62(s br), 6.57(s br), 6.18(s), 5.67(dd, 7Hz, 7Hz), 5.60(dd, 7Hz, 7Hz), 4.59(m), 4.02(d, 16Hz), 3.94(d, 17Hz), 3.91(s), 3.88(m), 3.74(dd, 15Hz, 7Hz), 3.53(dd, 15Hz, 9Hz), 3.39(dd, 12Hz, 12Hz), 3.03(dd, 13Hz, 12Hz), 0.69(d, 7Hz), 0.63(d, 7Hz) |
| 7 | 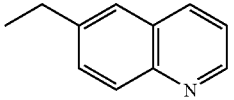 | 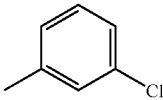 | R_f=0.45(T 4:1). δ=8.84(m), 8.12(d, 9Hz), 8.07(d, 8Hz), 8.00(d, 9Hz), 7.97(d, 9Hz), 7.90(d, 8Hz), 7.83(d, 8Hz), 7.76(d, 9Hz), 7.04(dd, 8Hz, 8Hz), 6.69(s), 6.68(s), 6.57(s br), 6.33(s br), 5.62(dd, 8Hz, 8Hz), 5.48(dd, 7Hz, 7Hz), 4.61(m), 4.00(d, 15Hz), 3.92(m), 3.89(d, 15Hz), 2.78(dd, 11Hz, 12Hz), 0.62(d, 7Hz), 0.58(d, 7Hz) |
| 8 | 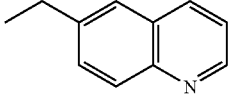 | 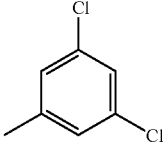 | R_f=0.60(T). δ=8.84(dd, 4Hz, 2Hz), 7.98(d, 9Hz), 7.89(d, 8Hz), 7.85(d, 8Hz), 7.76(d, 8Hz), 7.53(m), 7.41(dd, 7Hz, 7Hz), 7.28(m), 7.17(s), 7.13(m), 6.53(s), 6.49(s br), 6.29(s br), 5.91(m), 5.60(dd, 8Hz, 8Hz), 5.57(s br), 5.45(s br), 5.44(dd, 7Hz, 7Hz), 4.62(), 4.01(d, 15Hz), 3.97(m), 3.90(d, 16Hz), 3.41(dd, 15Hz, 7Hz), 2.78(dd, 13Hz, 11Hz), 1.91(m), 0.68(d, 7Hz), 0.62(d, 7Hz) |
| 9 | 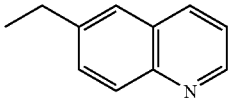 | 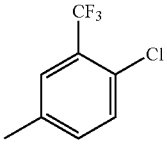 | R_f=0.55(T). δ=8.78(dd, 4Hz, 2Hz), 7.97(d, 8Hz), 7.88(d, 9Hz), 7.83(d, 7Hz), 7.81(d, 7Hz), 7.69(d, 9Hz), 7.57(s), 7.52(s), 7.47(dd, 7Hz, 8Hz), 7.23(d, 7Hz), 7.20(dd, 8Hz, 4Hz), 7.02(s), 6.85(s br), 6.81(s br), 6.37(s br), 6.19(s br), 5.86(s), 5.66(dd, 9Hz, 6Hz), 5.48(dd, 7Hz, 8Hz), 4.54(m), 4.01(m), 3.94(d, 15Hz), 3.88(d, 15Hz), 3.55(dd, 15Hz, 7Hz), 3.37(dd, 15Hz, 9Hz), 2.85(ddd, 14Hz, 9Hz, 3Hz), 0.62(d, 7Hz), 0.49(d, 7Hz) |
| 10 | 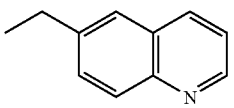 | 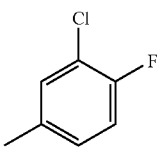 | R_f=0.30(T 4:1). δ=8.89(d, 4Hz), 8.85(d, 3Hz), 8.01(d, 8Hz), 7.99(d, 8Hz), 7.90(d, 8Hz), 7.86(d, 8Hz), 7.77(d, 8Hz), 6.87(dd, 8Hz, 8Hz), 6.45(s br), 6.23(s br), 5.97(s br), 5.61(dd, 8Hz, 8Hz), 5.46(dd, 7Hz, 7Hz), 5.39(s), 4.63(m), 4.00(d, 15Hz), 3.89(d, 14Hz), 2.80(dd, 13Hz, 11Hz), 0.66(d, 7Hz), 0.59(d, 7Hz) |
| 11 | 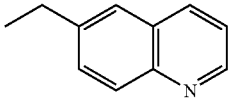 | 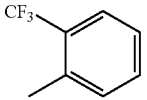 | R_f=0.40(T 4:1). δ=9.12(d, 5Hz), 9.08(d, 4Hz), 8.60(d, 8Hz), 8.45(d, 9Hz), 8.40(d, 9Hz), 8.39(s), 8.39(s), 8.37(d, 10Hz), 8.02(d, 8Hz), 7.90(d, 7Hz), 7.87(s), 7.77(d, 8Hz), 7.38(d, 8Hz), 7.18(d, 8Hz), 6.65(s br), 6.40(s br), 6.07(s), 5.89(s br), 5.81(s br), 5.60(dd, 8Hz, 8Hz), 5.54(dd, 8Hz, 8Hz), 4.57(m), 3.98(d, 16Hz), 3.90(d, 16Hz), 3.00(dd, 12Hz, 12Hz), 0.68(d, 7Hz), 0.58(d, 7Hz) |

TABLE 1-continued

| EX | R₂ | R₃ | DATA |
|---|---|---|---|
| 12 | ethyl-quinoline | 3,4-difluorophenyl | R$_f$=0.34(E two times). δ=8.85(dd, 4Hz, 2Hz), 8.12(d, 8Hz), 8.07(d, 9Hz), 7.99(d, 8Hz), 7.98(d, 9Hz), 7.90(d, 8Hz), 7.84(d, 8Hz), 7.77(d, 8Hz), 7.64(m), 7.54(m), 7.42(dd, 8Hz, 8Hz), 7.28(d, 7Hz), 7.21(dd, 8Hz, 4Hz), 7.10(dd, 9Hz, 9Hz), 6.60(m), 6.51(d, 9Hz), 6.43(s br), 6.33(s br), 6.20(s, br), 5.99(s), 5.60(dd, 8Hz, 8Hz), 5.46(dd, 7Hz, 8Hz), 5.37(s br), 4.64(m), 4.00(d, 15Hz), 3.89(d, 15Hz), 3.52(m), 3.41(dd, 15Hz, 8Hz), 2.79(dd, 13Hz, 11Hz), 0.66(d, 7Hz), 0.60(d, 7Hz) |
| 12a | ethyl-quinoline | 3-cyanophenyl | R$_f$=0.75(T 4:1). δ=8.85(d, 3Hz; Ar), 8.02(d, 8Hz; ar), 7.99(d, 8Hz; ar), 7.88(2d, 8Hz; ar), 7.77(d, 8Hz; ar), 7.66(s; ar), 7.56(s; ar), 7.29(s; 3-H A) 6.43(s br; NH A), 6.25(s br; NH B), 6.01(s; 3-H B), 5.72(s br; NH B), 5.61(t, 8Hz; B), 5.56(s br; NH A), 5.47(t, 8Hz; A), 4.63(m; B), 4.00(d, 15Hz), 3.90(d, 15Hz), 3.43(dd, 15Hz, 8Hz; A), 2.83(dd, 10Hz, 4Hz; A), 0.62(d, 7Hz; 5-Me A), 0.54(d, 7Hz; 5-Me B) |
| 12b | ethyl-quinoline | 3-(pyrimidin-5-yl)phenyl | R$_f$=0.25(T). NMR in MeOD: δ=9.2-8.85(m; ar), 8.97(s; ar) 8.1-7.1(m; ar), 7.20(s; 3-H A), 6.91(s, 3-H B), 4.41(m; 5 B), 3.97(m; 5 A), 0.63(d, 7Hz; 5-Me A), 0.45(d, 7Hz; 5-Me B) |
| 12c | ethyl-quinoline | 3-(trifluoromethoxy)phenyl | R$_f$=0.40(T 4:1). δ=8.88(dd, 4Hz, 1.5Hz; ar B), 8.84(dd, 4Hz, 1.5Hz; ar A), 8.10/8.07(2d, 9Hz; ar B) 8.00/7.97(2d, 9Hz; ar A), 7.90/7.83/7.76(3d, 8Hz, ar), 7.32(s; ar), 7.15(s; ar), 7.01/6.77(2d, 8Hz), 6.55(s br; NH A), 6.32(s br; NH B), 6.03(s; 3-H B), 5.66(t, 8Hz; alpha-H B), 5.59(s br, NH B), 5.50(t, 7.5Hz; alpha-H A), 5.49(s br; NH A), 4.63(m; 5 B), 3.93(m; 5 A), 4.00(d, 15Hz), 3.89(d, 15Hz), 2.80(dd, 11Hz, 13Hz), 0.57(d, 7Hz; 5-Me A), 0.54(d, 7Hz; 5-Me B) |
| 13 | ethyl-benzodioxole | 3-fluorophenyl | R$_f$=0.67(T). δ=8.01(d, 8Hz), 7.88(d, 8Hz), 7.77(d, 8Hz), 7.59(ddd, 8Hz), 7Hz, 1Hz), 7.52(dd, 7Hz, 7Hz), 7.43(dd, 8Hz, 8Hz), 7.31(d, 7Hz), 7.27(s), 7.04(d, 8Hz), 6.96(d, 9Hz), 6.75(d, 8Hz), 6.73(d, 1Hz), 6.67(m), 6.52(d, 8Hz), 6.43(d, 8Hz), 6.36(s br, NH), 5.98(s), 5.84(d, 1Hz), 5.75(d, 1Hz), 5.66(dd, 8Hz, 8Hz), 5.58(s br, NH), 5.47(dd, 7Hz, 7Hz), 4.58(m), 3.89(m), 3.73(d, 15Hz), 3.60(d, 15Hz), 3.35(d, 15Hz), 3.30(d, 13Hz), 2.77(dd, 13Hz, 11Hz), 0.60(d, 7Hz), 0.56(d, 7Hz) |
| 14 | ethyl-benzodioxole | 3-chlorophenyl | R$_f$=0.55(T 4:1). δ=8.01(d, 8Hz), 7.88(d, 8Hz), 7.78(d, 8Hz), 6.43(d, 8Hz), 5.96(s br), 5.87(d, 1Hz), 5.84(d, 1Hz), 5.8(d, 1Hz), 5.75(d, 1Hz), 5.66(dd, ~7.5Hz, ~7.5Hz), 5.45(dd, ~7.5Hz, ~7.5Hz), 4.58(ddq, 7Hz, 13Hz), 3.89(ddq, 7Hz, 12Hz, 6Hz), 2.77(dd, 14Hz, 11Hz), 0.61(d, 7Hz), 0.55(d, 7Hz) |

TABLE 1-continued

| EX | R$_2$ | R$_3$ | DATA |
|----|-------|-------|------|
| 15 | 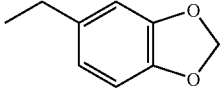 | 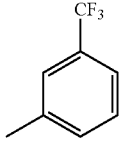 | R$_f$=0.75(T). δ=7.94(d, 8Hz), 7.80(d, 8Hz), 7.70(d, 8Hz), 7.70(d, 8Hz), 7.51(ddd, 8Hz, 7Hz, 1Hz), 7.16(d, 9Hz), 6.77(s), 6.72(s), 6.65(m), 6.45(d, 8Hz), 6.36(d, 8Hz), 6.27(s br), 5.94(s br), 5.79(d, 1Hz), 5.76(d, 1Hz), 5.74(d, 1Hz), 5.68(d, 1Hz), 5.63(dd, 8Hz, 8Hz), 5.58(s br), 5.44(s br), 5.41(dd, 7Hz, 7Hz), 4.50(m), 3.83(m), 3.67(d, 15Hz), 3.53(d, 15Hz), 3.39(dd, 15Hz, 7Hz), 3.19(d, 15Hz), 2.89(d, 16Hz), 2.72(dd, 13Hz, 11Hz), 0.46(d, 7Hz), 0.39(d, 7Hz) |
| 16 | 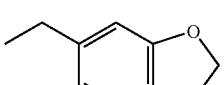 | 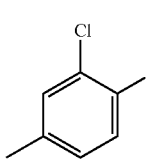 | R$_f$=0.53(E). δ=8.01(d, 8Hz), 7.89(d, 8Hz), 7.78(d, 8Hz), 7.60(ddd, 8Hz, 7Hz, 1Hz), 7.53(ddd, 8Hz, 7Hz, 1Hz), 7.43(dd, 8Hz, 7Hz), 7.43(dd, 8Hz, 7Hz), 7.36(d, 7Hz), 7.31(d, 8Hz), 7.21(s), 7.07(d, 9Hz), 6.97(dd, 8Hz, 9Hz), 6.53(dd, 8Hz, 1Hz), 6.45(s br), 6.45(d, 8Hz), 6.25(s br), 5.92(s), 5.88(d, 1Hz), 5.85(d, 1Hz), 5.82(d, 1Hz), 5.76(d, 1Hz), 5.65(dd, 8Hz, 8Hz), 5.43(dd, 7Hz, 7Hz), 5.36(s br), 4.59(m), 3.92(m), 3.74(d, 15Hz), 3.61(d, 15Hz), 3.31(d, 15Hz), 2.78(dd, 13Hz, 11Hz), 0.64(d, 7Hz), 0.57(d, 7Hz) |
| 16a | 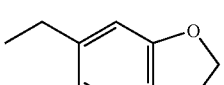 | 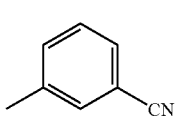 | R$_f$=0.31(T 4:1). δ=8.01(d, 8Hz; ar), 7.89(d, 8Hz; ar), 7.79(d, 8Hz; ar), 7.43(ddd, 8Hz, 5Hz, 5Hz), 7.25(s; H-3 A), 6.75(d, 8Hz), 6.73(d, 1Hz), 6.66(d, 8Hz), 6.52(d, 8Hz), 6.46(d, 8Hz), 6.41(s; br NH A), 6.26(s; br NH B), 5.97(s; H-3 B), 5.85/5.77(2s; OCH$_2$O A), 5.66(t, 8Hz), 5.59(s; br NH B), 5.47(s; br NH A), 5.45(t, 8Hz), 4.59(m; 5 B), 3.95(m; 5 A), 3.74(d, 15Hz), 3.62(d, 15Hz), 3.29(d, 15Hz), 2.81(ddd, 8Hz, 7Hz, 4Hz; 7), 0.60(d, 7Hz; 5-Me A), 0.49(d, 7Hz; 5-Me B) |
| 16b | 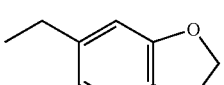 | 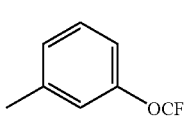 | R$_f$=0.68(CH$_2$Cl$_2$/i-PrOH 20:1). δ=8.02(d, 8Hz; ar), 7.88(d, 8Hz; ar), 7.78(d, 8Hz; ar), 7.59(m; ar), 7.52(m; ar), 7.43(m; ar), 7.12(s; 3-H A), 6.73(m), 6.52(d, 8Hz), 6.44(d, 8Hz), 6.45(s; br NH A), 6.35(s; br NH B), 5.98(s; H-3 B), 5.84/5.76(2s; OCH$_2$O A), 5.86/5.80(2s; OCH$_2$O B), 5.69(t, 8Hz), 5.57(s; br NH B), 5.48(t, 8Hz), 5.46(s; br NH A), 4.58(m; 5 B), 3.89(m; 5 A), 3.73(d, 15Hz), 3.60(d, 15Hz), 3.29(d, 15Hz), 2.79(m), 0.56(d, 7Hz; 5-Me A), 0.51(d, 7Hz; 5-Me B) |
| 17 | 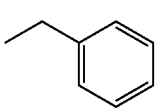 | 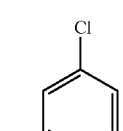 | R$_f$=0.47(E). δ=8.00(d, 8Hz), 7.89(d, 8Hz), 7.89(d, 7Hz), 7.79(d, 8Hz), 7.61(ddd, 8Hz, 7Hz, 1Hz), 7.54(ddd, 8Hz, 7Hz, 1Hz), 7.45(dd, 8Hz, 7Hz), 7.05(d, 7Hz), 6.66(s), 6.64(s), 6.59(s br), 6.33(s br), 5.96(s), 5.62(dd, 8Hz, 8Hz), 5.55(s br), 5.48(s br), 5.45(dd, 7Hz, 7Hz), 4.59(m), 3.86(d, 15Hz), 3.70(d, 14Hz), 3.58(dd, 16Hz, 8Hz), 3.42(dd, 15Hz, 8Hz), 2.62(dd, 13Hz, 11Hz), 1.80(ddd, 15Hz, 6Hz, 6Hz), 0.59(d, 7Hz), 0.54(d, 7Hz) |

TABLE 1-continued

| EX | R₂ | R₃ | DATA |
|---|---|---|---|
| 18 | 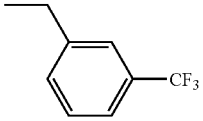 | 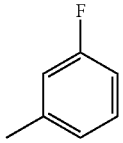 | R$_f$=0.75(T). δ=8.04(d, 8Hz), 7.89(d, 8Hz), 7.77(d, 8Hz), 7.59(ddd, 8Hz, 7Hz, 1Hz), 7.52(dd, 8Hz, 7Hz), 7.27(s), 6.68(d, 8Hz), 6.60(s br), 6.56(d, 8Hz), 6.33(s br), 5.90(s), 5.68(dd, 8Hz, 8Hz), 5.60(s br), 5.54(dd, 7Hz, 7Hz), 5.50(s br), 4.57(m), 3.80(m), 3.80(d, 15Hz), 3.70(d, 15Hz), 3.30(dd, 13Hz, 11Hz), 2.83(dd, 13Hz, 11Hz), 0.59(d, 7Hz), 0.58(d, 7Hz) |
| 19 | 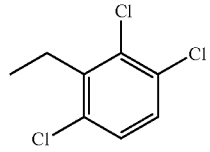 | 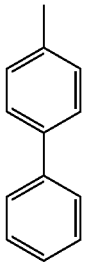 | R$_f$=0.47(T 4:1). δ=8.07(d, 8.5Hz), 8.01(d, 8.5Hz), 7.86(d, 8Hz), 7.78(d, 8Hz), 7.74(d, 8Hz), 7.55(d, 8Hz), 6.68(s, br), 6.34(s, br), 6.28(s), 5.63(dd, 5.5Hz, 9Hz), 5.55(dd, 8Hz, 8Hz), 5.48(s, br), 4.64(m), 4.41(d, 16.5Hz), 4.14(d, 16.5Hz), 4.02(d, 16.5Hz), 3.97(m), 3.68(dd, 8.5Hz, 8.5Hz), 3.32(dd, 11Hz, 14Hz), 0.79(d, 7Hz), 0.70(d, 7Hz) |
| 20 | 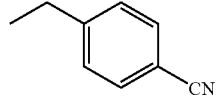 | 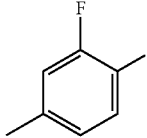 | R$_f$=0.55(E two times). δ=8.05(d, 8Hz), 7.93(d, 8Hz), 7.79(d, 8Hz), 7.63(ddd, 8Hz, 7Hz, 1Hz), 7.44(dd, 8Hz, 8Hz), 7.20(s), 7.18(d, 8Hz), 7.06(d, 8Hz), 6.52(s br), 5.79(s), 5.63(dd, 9Hz, 6Hz), 5.45(s br), 4.56(m), 3.78(d, 15Hz), 3.66(d, 15Hz), 2.70(dd, 14Hz, 11Hz), 0.64(d, 7Hz), 0.60(d, 7Hz) |
| 21 | 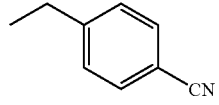 | 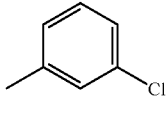 | R$_f$=0.55(T 4:1). δ=7.98(d, 8Hz), 7.95(d, 8Hz), 7.84(d, 7Hz), 7.81(d, 9Hz), 7.71(d, 8Hz), 7.35(dd, 8Hz, 8Hz), 7.24(d, 8Hz), 7.16(s), 7.08(d, 8Hz), 6.98(d, 8Hz), 6.69(d br, 8Hz), 6.66(s), 6.59(s br), 6.28(s br), 5.73(s), 5.61(dd, 8Hz, 7Hz), 5.58(dd, 9Hz, 6Hz), 5.52(s br), 4.45(m), 3.70(d, 15Hz), 3.62(m), 3.58(d, 15Hz), 3.41(d, 15Hz), 3.22(dd, 12Hz, 12Hz), 2.61(dd, 13Hz, 11Hz), 1.98(s), 1.79(s), 0.53(d, 7Hz), 0.49(d, 7Hz) |
| 22 | 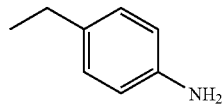 | 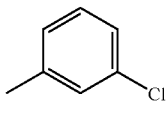 | R$_f$=0.40(T 4:1). δ=7.96(d, 9Hz), 7.95(d, 8Hz), 7.84(d, 8Hz), 7.80(d, 8Hz), 7.72(d, 8Hz), 7.48(d, 7Hz), 7.40(dd, 8Hz, 8Hz), 7.22(d, 7Hz), 6.98(d, 8Hz), 6.73(d, 8Hz), 6.11(d, 8Hz), 5.92(s), 5.52(dd, 7Hz, 6Hz), 5.42(s br), 4.50(m), 3.79(m), 3.65(d, 15Hz), 3.49(d, 14Hz), 3.41(dd, 8Hz, 16Hz), 2.52(dd, 12Hz, 12Hz), 0.51(d, 7Hz), 0.45(d, 7Hz) |
| 23 | 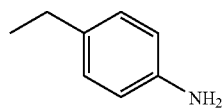 | 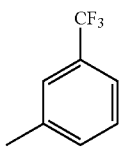 | R$_f$=0.57(T). δ=7.99(d, 8Hz), 7.97(d, 8Hz), 7.84(d, 8Hz), 7.73(d, 8Hz), 7.54(ddd, 8Hz, 7Hz, 1Hz), 7.45(s), 6.97(d, 8Hz), 6.75(d, 8Hz), 6.59(d, 8Hz), 6.17(d, 8Hz), 5.96(s), 5.76(s br), 5.61(dd, 8Hz, 7Hz), 5.46(dd, 7Hz, 7Hz), 4.50(m), 3.83(m), 3.67(d, 15Hz), 3.51(d, 15Hz), 2.56(dd, 13Hz, 10Hz), 0.45(d, 7Hz), 0.39(d, 7Hz) |
| 24 | 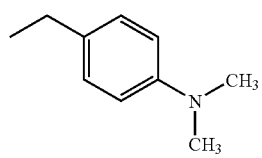 | 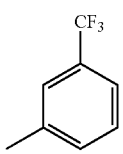 | R$_f$=0.53(T 4:1). δ=7.97(d, 8Hz), 7.84(d, 7Hz), 7.74(d, 8Hz), 7.31(s), 7.24(d, 7Hz), 7.06(d, 9Hz), 6.80(d, 8Hz), 6.73(s), 6.59(d, 9Hz), 6.53(s br), 6.16(d, 9Hz), 6.05(s), 5.61(dd, 8Hz, 8Hz), 5.46(dd, 7Hz, 7Hz), 5.33(s br), 5.27(s br), 4.55(m), 3.85(m), 3.73(d, 15Hz), 3.53(d, 15Hz), 3.22(d, 15Hz), 2.73(s), 2.58(s), 0.45(d, 7Hz), 0.38(d, 7Hz) |

TABLE 1-continued

| EX | R₂ | R₃ | DATA |
|----|----|----|------|
| 25 | 3-aminophenyl-ethyl | 3-chlorophenyl | R_f=0.65(T; free base). δ=7.98(d, 8Hz), 7.85(d, 7Hz), 7.77(d, 8Hz), 7.75(d, 8Hz), 7.18(m), 6.58(s br), 6.31(s br), 6.00(s), 5.35(m), 4.93(m), 4.45(m), 3.44(d, 15Hz), 3.22(dd, 13Hz, 11Hz), 0.58(d, 7Hz), 0.50(d, 7Hz) |
| 26 | 4-(3-carboxypropanoylamino)phenyl-ethyl | 3-(trifluoromethyl)phenyl | R_f=0.31(T) tailing. δ=9.00(s), 8.79(s), 7.97(d, 9Hz), 7.83(d, 8Hz), 7.72(d, 8Hz), 7.15(s), 7.10(d, 8Hz), 7.02(d, 8Hz), 6.86(s), 6.65(s br), 6.16(s br), 6.00(s br), 5.89(s), 5.64(dd, 8Hz, 8Hz), 5.41(dd, 7Hz, 7Hz), 4.50(m), 3.86(m), 3.72(d, 15Hz), 3.62(d, 15Hz), 3.26(d, 15Hz), 2.70(dd, 13Hz, 11Hz), 2.53(m), 1.82(m), 0.46(d, 7Hz), 0.39(d, 7Hz) |
| 27 | 4-(3-carboxypropanoylamino)phenyl-ethyl | 3-chlorophenyl | R_f=0.30(T). δ=8.15(d, 9Hz), 8.09(d, 8Hz), 7.91(d, 8Hz), 7.91(d, 8Hz), 7.80(d, 8Hz), 7.52(m), 7.40(dd, 8Hz, 7Hz), 7.36(d, 8Hz), 7.13(d, 8Hz), 6.95(s), 6.85(d, 8Hz), 6.65(s), 5.82(s), 5.79(dd, 10Hz, 6Hz), 5.59(dd, 10Hz, 6Hz), 4.47(m), 4.05(m), 3.76(m), 3.48(dd, 14Hz, 10Hz), 2.92(dd, 14Hz, 11Hz), 2.62(m), 2.51(m), 0.54(d, 7Hz), 0.46(d, 7Hz) |
| 28 | 4-(3-carboxypropanoylamino)phenyl-ethyl | 3-chlorophenyl | R_f=0.65(T). δ=8.42(s), 8.37(s), 7.98(d, 8Hz), 7.84(d, 8Hz), 7.74(d, 8Hz), 7.55(dd, 7Hz, 7Hz), 7.40(d, 8Hz), 7.35(d, 7Hz), 7.13(s), 6.82(s), 6.80(s), 6.67(s br), 6.29(s br), 5.96(s), 5.37(s br), 4.99(s br), 4.48(m), 3.78(d, 15Hz), 3.22(dd, 12Hz, 13Hz), 0.57(d, 7Hz), 0.49(d, 7Hz) |
| 29 | 4-(aminoacetylamino)phenyl-ethyl | 3-chlorophenyl | R_f=0.45(RP-8, MeOH/H₂O/TFA 70:30:1). δ=8.18(d, 9Hz), 8.09(d, 8Hz), 7.91(d, 8Hz), 7.90(d, 8Hz), 7.79(d, 8Hz), 7.49(d, 8Hz), 7.38(dd, 8Hz, 8Hz), 6.93(s), 6.88(s), 6.87(d, 8Hz), 6.59(s), 5.81(dd, 10Hz, 6Hz), 5.78(s), 5.56(dd, 10Hz, 6Hz), 4.44(m), 4.07(m), 3.81(s), 3.77(s), 3.72(s), 3.23(dd, 13Hz, 11Hz), 3.01(dd, 14Hz, 10Hz), 0.52(d, 7Hz), 0.44(d, 7Hz) |
| 30 | 3-(aminoacetylamino)phenyl-ethyl | 3-chlorophenyl | δ=9.84(s br), 9.79(s br), 7.98(d, 8Hz), 7.84(d, 8Hz), 7.74(d, 8Hz), 7.53(dd, 7Hz, 7Hz), 7.47(dd, 7Hz, 8Hz), 7.40(d, 7Hz), 7.25(s), 6.95(dd, 7Hz, 8Hz), 6.80(d, 8Hz), 6.74(s br), 6.24(s br), 5.95(s), 5.44(s br), 4.96(s br), 4.44(m), 3.19(dd, 13Hz, 12Hz), 2.73(dd, 11Hz, 11Hz), 0.54(d, 7Hz), 0.48(d, 7Hz) |

TABLE 1-continued

| EX | R₂ | R₃ | DATA |
|---|---|---|---|
| 31 | 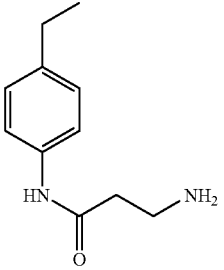 | 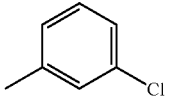 | R_f=0.52(BuOH/MeOH/H₂O/AcOH 10:5:2:1). δ=8.16(d, 8Hz), 8.09(d, 9Hz), 7.91(d, 8Hz), 7.80(d, 8Hz), 7.60(d, 9Hz), 7.57(ddd, 8Hz, 7Hz, 1Hz), 7.46(m), 7.40(dd, 8Hz, 7Hz), 7.29(s), 7.18(d, 8Hz), 6.94(s), 6.89(d, 8Hz), 6.63(s), 5.81(s), 5.79(dd, 10Hz, 6Hz), 5.57(dd, 10Hz, 6Hz), 4.46(m), 4.08(m), 3.78(s), 3.70(dd, 15Hz, 6Hz), 3.58(m), 3.48(dd, 15Hz), 10Hz), 3.23(dd, 6Hz, 6Hz), 3.11(dd, 13Hz, 7Hz), 2.99(dd, 13Hz, 11Hz), 2.75(dd, 6Hz, 6Hz), 2.62(dd, 13Hz, 7Hz), 0.53(d, 7Hz), 0.45(d, 7Hz) |
| 32 | 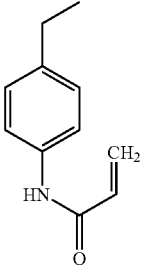 | 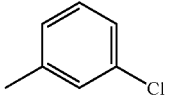 | R_f=0.65(T). δ=8.04(m br), 7.94(d, 7Hz), 7.81(d, 8Hz), 6.73(s), 6.62(s br), 6.36(d, 16Hz), 6.30(d, 17Hz), 5.96(s), 5.73(d, 8Hz), 5.65(d, 9Hz), 5.55(m Br), 4.57(m), 0.59(d), 0.55(d, 6Hz) |
| 33 | 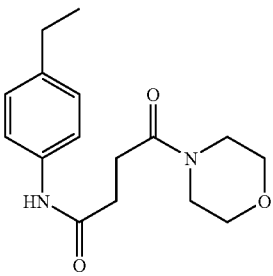 | 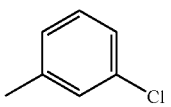 | R_f=0.42(T). δ=8.04(d, 8Hz), 8.00(d, 9Hz), 7.93(d, 8Hz), 7.88(d, 8Hz), 7.80(d, 8Hz), 7.76(s), 7.07(d, 8Hz), 6.98(d, 8Hz), 6.94(s), 6.66(s), 6.62(s br), 5.96(s), 5.59(dd, 8Hz, 8Hz), 5.51(dd, 7Hz, 7Hz), 4.58(m), 3.83(m), 3.76(d, 15Hz), 3.64(m), 3.58(m), 3.47(m), 2.62(m), 0.58(d, 7Hz), 0.54(d, 7Hz) |
| 34 | 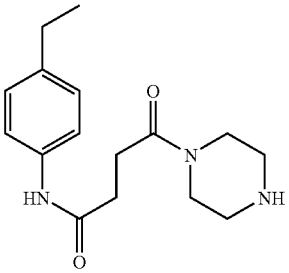 | 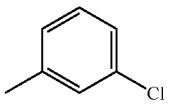 | R_f=0.37(RP-8 MeOH/H₂O/TFA 70:30:12). δ=9.90(s br), 8.22(d, 8Hz), 8.18(d, 8Hz), 7.95(d, 8Hz), 7.82(d, 8Hz), 7.51(d, 8Hz), 7.34(m), 7.25(s), 7.11(d, 8Hz), 7.02(d, 9Hz), 6.69(s), 5.60(dd, 10Hz, 5Hz), 5.45(dd, 10Hz, 5Hz), 4.35(m), 4.14(dd, 5Hz, 5Hz), 4.06(m), 3.76(d, 16Hz), 3.70(d, 15Hz), 0.48(d, 6Hz), 0.39(d, 7Hz) |
| 35 | 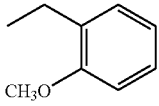 | 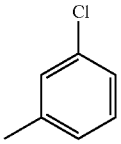 | R_f=0.42(E). δ=8.04(d, 9Hz), 7.89(d, 8Hz), 7.77(d, 8Hz), 7.59(ddd, 8Hz, 7Hz, 1Hz), 7.52(ddd, 8Hz, 7Hz, 1Hz), 7.42(dd, 8Hz, 7Hz), 6.84(d, 8Hz), 6.66(dd, 7Hz, 7Hz), 6.60(s br), 6.34(s br), 6.13(s), 5.59(dd, 8Hz, 8Hz), 5.44(dd, 7Hz, 7Hz), 5.37(s br), 4.59(m), 3.88(m), 3.80(s), 3.74(s), 3.72(d, 6Hz), 3.42(dd, 15Hz, 8Hz), 3.31(ddd, 13Hz, 10Hz, 2Hz), 2.92(dd, 13Hz, 11Hz), 0.63(d, 7Hz), 0.53(d, 7Hz) |

TABLE 1-continued

| EX | R2 | R3 | DATA |
|---|---|---|---|
| 36 | 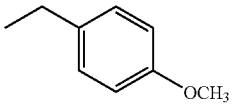 | 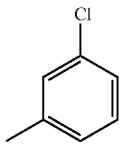 | Rf=0.44(E). δ=7.97(d, 9Hz), 7.83(d, 9Hz), 7.73(d, 8Hz), 7.52(dd, 8Hz, 8Hz), 7.35(dd, 7Hz, 7Hz), 6.83(d, 9Hz), 6.62(d, 8Hz), 6.58(s br), 6.49(s), 6.32(d, 9Hz), 5.89(s), 5.57(dd, 8Hz, 7Hz), 5.47(dd, 7Hz, 7Hz), 5.41(s br), 4.51(m), 3.71(s), 3.60(s), 3.56(d, 9Hz), 3.38(s), 2.53(dd, 13Hz, 11Hz), 1.71(ddd, 15Hz, 6Hz, 6Hz), 0.51(d, 7Hz), 0.46(d, 7Hz) |
| 37 | 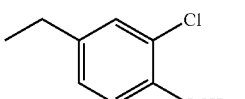 | 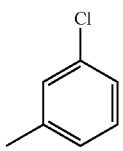 | Rf=0.37(E). δ=8.06(d, 8Hz), 8.01(d, 8Hz), 7.90(d, 8Hz), 7.81(d, 8Hz), 7.59(dd, 7Hz, 7Hz), 7.52(dd, 8Hz, 8Hz), 7.48(dd, 8Hz, 8Hz), 7.16(s), 6.86(dd, 8Hz, 7Hz), 6.80(d, 8Hz), 6.71(s), 6.69(dd, 8Hz, 2Hz), 6.65(s br), 6.36(s br), 6.07(d, 8Hz), 5.91(s), 5.66(dd, 8Hz, 8Hz), 5.60(dd, 7Hz, 7Hz), 5.51(s, br), 4.57(m), 3.76(s), 3.73(d, 15Hz), 3.52(s), 2.69(dd, 13Hz, 11Hz), 0.60(d, 7Hz), 0.57(d, 7Hz) |
| 38 | —CH3 | 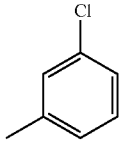 | Rf=0.46(toluene/i-PrOH 4:1). δ=8.07(d, 8Hz), 8.00(d, 8Hz), 7.87(dd, 8Hz, 2Hz), 7.76(d, 8Hz), 7.57(ddd, 8Hz, 7Hz, 1.5Hz), 7.50(ddd, 8Hz, 7Hz, 1Hz), 7.43(dd, 7Hz, 7Hz), 7.23(m), 6.68(s br,), 6.42(s br), 5.79(s), 5.70(dd, 10Hz, 6Hz), 5.61(s, br), 5.52(dd, 8Hz, 8Hz), 4.55(m), 3.68(m), 3.34(dd), 3.10(dd, 13.5Hz, 11Hz), 2.09(s), 0.64(d, 7Hz), 0.59(d, 7Hz) |

Preparation of Starting Materials

Naphythylalanine Amide (Compound A1)

Naphthalene-1-carboxylic acid is dissolved in dry THF and 5 equiv. of borane dimethylsulfide complex are added. The mixture obtained is stirred at rt, diluted with EtAc, washed with 1N HCl and 5% NaHCO3 solution, dried and solvent is evaporated. (Naphthalene-1-yl)-methanol is obtained, which is dissolved in CH2Cl2. To the solution obtained 1.5 equiv. of Dess-Martin reagent are added at rt. The mixture obtained is diluted with EtAc, extracted with 1N HCl and 5% NaHCO3-solution, dried and solvent is evaporated. Naphthalene-1-carboxaldehyde is obtained and dissolved with 1 equiv. of racemic-Boc-α-phosphonoglycine trimethylester in CH2Cl2 and 1.1 equiv. of DBU are added. The mixture obtained is stirred at rt and treated in sequence with 1N HCl and 5% NaHCO3 solution. The phases obtained are separated, the organic phase obtained is dried and solvent is evaporated. 2-Boc-amino-3-(naphthalene-1-yl)-acrylic acid methyl ester (cis/trans mixture) is obtained, is dissolved in MeOH/H2O at pH 6.5 (phosphate buffer) and 20 w/w % of 10% Pd/C are added. The mixture obtained is hydrogenated at rt and 50 bar, the catalyst is filtered off and from the filtrate obtained solvent is evaporated. Racemic naphythylalanine methylester is obtained, dissolved in methanolic NH3 and stirred. The mixture obtained is subjected to extractive work up. Racemic naphythylalanine amide is obtained.

Test Example

Inhibition of Allergic Contact Dermatitis (ACD) In Vivo a. Method:

Groups of 8 female mice are sensitized epicutaneously with 50 μl of 2% oxazolone on the shaved ventral abdomen (day 1) and challenged with 10 μl of 0.2% oxazolone on the inner surface of the right ear (day 8). The unchallenged left ears serve as normal controls and dermatitis is evaluated from the difference in pinnal weight which is taken as a measure of inflammatory swelling (day 9). In addition, activity of myeloperoxidase (MPO) serving as a measure of leukocyte influx in ear homogenates are determined as described by Bradley et al., J. Invest. Dermatol; 78:206-209 (1982). The animals are treated orally 2 hours after challenge with the test compound of example 10. Activity is calculated as the percentage of inhibition of inflammatory auricular swelling and of MPO activity relative to animals treated with the vehicle alone. For comparison mice are treated intraperitoneally with 100 μl monoclonal anti-mouse LFA-1 antibody 1 hour before challenge and evaluated as described.

b) Results

Oral treatment with a single dose of 0.01-10.0 mg/kg of a compound of example 10 results in an inhibition of the inflammatory response by 40-50%. Inhibition of swelling compared with inhibition of MPO activity is observed. Treatment with 50-200 μg/mouse anti-LFA-1 antibody results in an inhibition by 34-56%.

The invention claimed is:
1. A compound of formula

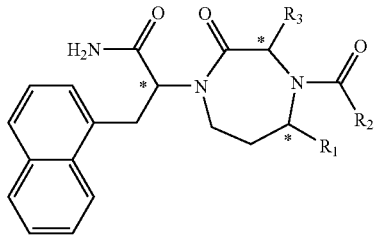

I wherein
R₁ is (C₁₋₄)alkyl;
R₂ is unsubstituted (C₁₋₄)alkyl or (C₁₋₄)alkyl substituted by unsubstituted or substituted
(C₆₋₁₈)aryl
wherein the aryl substitutients are
halogen, halo(C₁₋₄)alkyl, (C₁₋₄)alkoxy, cyano, amino, dimethylamino, carboxy (C₁₋₂)alkylcarbonylamino, amino(C₁₋₂)alkylcarbonylamino, (C₂₋₄)alkylenecarbonylamino, or heterocyclylcarbonyl (C₁₋₂)alkylcarbonylamino, wherein heterocyclyl has 6 ring members and 2 heteroatoms selected from N, and O; or (C₆₋₁₈)aryl annelated with heterocyclyl having 5 or 6 ring members and 1 to 4 heteroatoms selected from N, O, and S; and
wherein the substituents are
halogen
unsubstituted amino or amino substituted by one or two (C₁₋₄) alkyl,
cyano
(C₁₋₄) alkoxy, or
(C₁₋₆) haloalkyl, and
R₃ is (C₆₋₁₈)aryl one or morefold substituted by
halogen,
halo(C₁₋₆)alkyl
halo(C₁₋₆)alkoxy,
cyano,
phenyl, or
heterocyclyl having 5 to 6 ring members and 1 to 4 heteroatoms selected from N, O, and S.

2. A compound of claim 1 wherein
R₁ is methyl;
R₂ is methyl or
methyl substituted by
quinolinyl,
benzo[1,3]dioxolyl,
phenyl,
phenyl one or morefold substituted by halogen, halo (C₁₋₄)alkyl, (C₁₋₄)alkoxy, cyano, amino, dimethylamino, carboxy(C₁₋₂)alkylcarbonylamino, amino (C₁₋₂)alkylcarbonylamino, (C₂₋₄)alkylenecarbonylamino, or heterocyclylcarbonyl(C₁₋₂) alkylcarbonylamino, wherein heterocyclyl has 6 ring members and 2 heteroatoms selected from N, and O;
R₃ is phenyl one or morefold, substituted by
halogen,
halo(C₁₋₂)alkyl,
halo(C₁₋₂)alkoxy,
cyano,
phenyl, or
heterocyclyl, including aromatic, having 6 ring members and 2 nitrogen heteroatoms.

3. A compound of claim 1 of formula

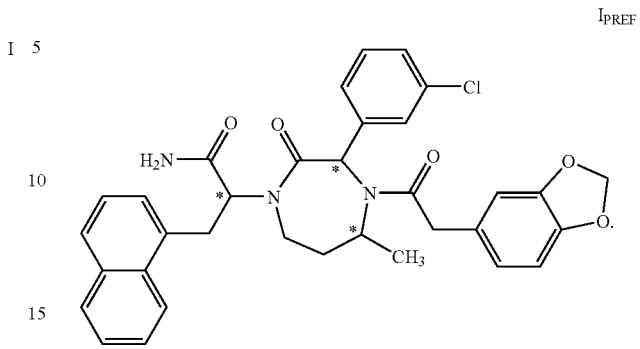

I_PREF

4. A compound of claim 1 in the form of a pharmaceutically acceptable salt.
5. A pharmaceutical composition comprising a compound of formula I according to claim 1 in association with at least one pharmaceutical excipient.
6. A pharmaceutical composition according to claim 5, further comprising another pharmaceutically active agent selected from compounds active in immunodulating regimens or other anti-inflammatory agents.
7. A method for treatment of allergic contact dermatitis in a subject in need of such treatment, which method comprises administering to said subject an effective amount of a compound of formula I according to claim 1.
8. A method for treatment of allergic contact dermatitis in a subject in need of such treatment, wherein a compound of claim 1 is administered in combination with another pharmaceutically active agent selected from compounds active in immunodulatory regimens or other anti-inflammatory agents, either simultaneously or in sequence.
9. A compound selected from the group consisting of
2-[3-(3-Fluoro-phenyl)-5-methyl-2-oxo-4-(quinolin-6-yl-acetyl)-[1,4]diazepam-1-yl]-3-naphthalen-1-yl-propionamide,
2-[5-Methyl-2-oxo-4-(quinoline-6-yl-acetyl(3-trifluoromethyl-phenyl)-[1,4]diazepam-1-yl]-3-naphthalen-1-yl-propionamide,
2-[3-(4-Fluoro-phenyl)-5-methyl-2-oxo-4-(quinolin-6-yl-acetyl)-[1,4]diazepam-1-yl]-3-naphthalen-1-yl-propionamide,
2-[3-(2-Fluoro-phenyl)-5-methyl-2-oxo-4-(quinolin-6-yl-acetyl)-[1,4]diazepam-1-yl]-3-naphthalen-1-yl-propionamide,
2-[3-(3-Bromo-phenyl)-5-methyl-2-oxo-4-(2-quinolin-6-yl-acetyl)-[1,4]diazepam-1-yl]-3-naphthalen-1-yl-propionamide,
2-[3-Biphenyl-3-yl-5-methyl-2-oxo-4-(2-quinolin-6-yl-acetyl)-[1,4]diazepan-1-yl]-3-naphthalen-1-yl-propionamide,
2-[3-(3-Chloro-phenyl)-5-methyl-2-oxo-4-(2-quinolin-6-yl-acetyl)-[1,4]diazepan-1-yl]-3-naphthalen-1-yl-propionamide,
2-[3-(3,5-Dichloro-phenyl)-5-methyl-2-oxo-4-(2-quinolin-6-yl-acetyl)-[1,4]diazepan-1-yl]-3-naphthalen-1-yl-propionamide,
2-[3-(4-Chloro-3-trifluoromethyl-phenyl)-5-methyl-2-oxo-4-(2-quinolin-6-yl-acetyl)-[1,4]diazepan-1-yl]-3-naphthalen-1-yl-propionamide,
2-[3-(3-Chloro-4-fluoro-phenyl)-5-methyl-2-oxo-4-(2-quinolin-6-yl-acetyl)-[1,4]diazepan-1-yl]-3-naphthalen-1-yl-propionamide, 2-[5-Methyl-2-oxo-4-(2-quinolin-6-yl-acetyl)-3-(2-trifluoromethyl-phenyl)-[1,4]diazepan-1-yl]-3-naphthalen-1-yl-propionamide,
2-[3-(3,4-Difluoro-phenyl)-5-methyl-2-oxo-4-(2-quinolin-6-yl-acetyl)-[1,4]diazepan-1-yl]-3-naphthalen-1-yl-propionamide,
2-[3-(3-Cyano-phenyl)-5-methyl-2-oxo-4-(2-quinolin-6-yl-acetyl)-[1,4]diazepan-1-yl]-3-naphthalen-1-yl-propionamide,
2-[5-Methyl-2-oxo-3-(3-pyrimidin-5-yl-phenyl)-4-(2-quinolin-6-yl-acetyl)-[1,4]diazepan-1-yl]-3-naphthalen-1-yl-propionamide, e.g. (R)-2-[5-Methyl-2-oxo-3-(3-pyrimidin-5-yl-phenyl)-4-(2-quinolin-6-yl-acetyl)-[1,4]diazepan-1-yl]-3-naphthalen-1-yl-propionamide,
2-[5-Methyl-2-oxo-4-(2-quinolin-6-yl-acetyl)-3-(3-trifluoromethoxy-phenyl)-[1,4]diazepan-1-yl]-3-naphthalen-1-yl-propionamide,
2-[4-(2-Benzo[1,3]dioxol-5-yl-acetyl)-3-(3-fluoro-phenyl)-5-methyl-2-oxo-[1,4]diazepan-1-yl]-3-naphthalen-1-yl-propionamide,
2-[4-(2-Benzo[1,3]dioxo-5-yl-acetyl)-3-(3-chloro-phenyl)-5-methyl-2-oxo-[1,4]diazepan-1-yl]-3-naphthalen-1-yl-propionamide,
2-[4-(2-Benzo[1,3]dioxol-5-yl-acetyl)-5-methyl-2-oxo-3-(3-trifluoromethyl-phenyl)-[1,4]diazepan-1-yl]-3-naphthalen-1-yl-propionamide,
2-[4-(2-Benzo[1,3]dioxol-5-yl-acetyl)-3-(3-chloro-4-fluoro-phenyl)-5-methyl-2-oxo-[1,4]diazepan-1-yl]-3-naphthalen-1-yl-propionamide,
2-[4-(2-Benzo[1,3]dioxol-5-yl-acetyl)-3-(3-cyano-phenyl)-5-methyl-2-oxo-[1,4]diazepan-1-yl]-3-naphthalen-1-yl-propionamide,
2-[4-(2-Benzo[1,3]dioxol-5-yl-acetyl)-5-methyl-2-oxo-3-(3-trifluoromethoxy-phenyl)-[1,4]diazepan-1-yl]-3-naphthalen-1-yl-propionamide,
2-[3-(3-Chloro-phenyl)-5-methyl-2-oxo-4-phenylacetyl-[1,4]diazepan-1-yl]-3-naphthalen-1-yl-propionamide,
2-[3-(3-Fluoro-phenyl)-5-methyl-2-oxo-4-[(3-trifluoromethyl-phenyl)-acetyl]-[1,4]diazepan-1-yl]-3-naphthalen-1-yl-propionamide,
2-{3-Biphenyl-4-yl-5-methyl-2-oxo-4-[2-(2,3,6-trichloro-phenyl)-acetyl]-[1,4]diazepan-1-yl}-3-naphthalen-1-yl-propionamide,
2-[4-[2-(4-Cyano-phenyl)-acetyl]-3-(3,4-difluoro-phenyl)-5-methyl-2-oxo-[1,4]diazepan-1-yl]-3-naphthalen-1-yl-propionamide,
2-[3-(3-Chloro-phenyl)-4-[2-(4-cyano-phenyl)-acetyl]-5-methyl-2-oxo-[1,4]diazepan-1-yl]-3-naphthalen-1-yl-propionamide,
2-[4-[2-(4-Amino-phenyl)-acetyl]-3-(3-chloro-phenyl)-5-methyl-2-oxo-[1,4]diazepan-1-yl]-3-naphthalen-1-yl-propionamide,
2-[4-[2-(4-Amino-phenyl)-acetyl]-5-methyl-2-oxo-3-(3-trifluoromethyl-phenyl)-[1,4]diazepan-1-yl]-3-naphthalen-1-yl-propionamide,
2-[4-[2-(4-Dimethylamino-phenyl)-acetyl]-5-methyl-2-oxo-3-(3-trifluoromethyl-phenyl)-[1,4]diazepan-1-yl]-3-naphthalen-1-yl-propionamide,
2-[4-[2-(3-Amino-phenyl)-acetyl]-3-(3-chloro-phenyl)-5-methyl-2-oxo-[1,4]diazepan-1-yl]-3-naphthalen-1-yl-propionamide,
N-(4-{2-[4-(1-Carbamoyl-2-naphthalen-1-yl-ethyl)-7-methyl-3-oxo-2-(3-trifluoromethyl-phenyl)-[1,4]diazepan-1-yl]-2-oxo-ethyl}phenyl)-succinamic acid,
N-(4-{2-[4-(1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-succinamic acid,
N-(3-{2-[4-(1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-succinamic acid,
2-[4-{2-[4-(2-Amino-acetylamino)-phenyl]-acetyl}-3-(3-chloro-phenyl)-5-methyl-2-oxo-[1,4]diazepan-1-yl]-3-naphthalen-1-yl-propionamide,
2-[4-{2-[3-(2-Amino-acetylamino)-phenyl]-acetyl}-3-(3-chloro-phenyl)-5-methyl-2-oxo-[1,4]diazepan-1-yl]-3-naphthalen-1-yl-propionamide,
2-[4-{2-[4-(3-Amino-propionylamino)-phenyl]-acetyl}-3-(3-chloro-phenyl)-5-methyl-2-oxo-[1,4]diazepan-1-yl]-3-naphthalen-1-yl-propionamide,
N-(4-{2-[4-(1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-acrylamide,
N-(4-{2-[4-(1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-4-morpholin-4-yl-4-oxo-butyramide,
N-(4-{2-[4-(1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-4-oxo-4-piperazin-1-yl-butyramide,
2-{3-(3-Chloro-phenyl)-4-[2-(2-methoxy-phenyl)-acetyl]-5-methyl-2-oxo-[1,4]diazepan-1-yl}-3-naphthalen-1-yl-propionamide,
2-{3-(3-Chloro-phenyl)-4-[2-(4-methoxy-phenyl)-acetyl]-5-methyl-2-oxo-[1,4]diazepan-1-yl}-3-naphthalen-1-yl-propionamide,
2-[4-[2-(3-Chloro-4-methoxy-phenyl)-acetyl]-(3-(3-chloro-phenyl)-5-methyl-2-oxo-[1,4]diazepan-1-yl]-3-naphthalen-1-yl-propionamide and
2-[4-Acetyl-3-(3-chloro-phenyl)-5-methyl-2-oxo-[1,4]diazepam-1-yl]-3-naphthalen-1-yl propionamide.

10. A compound selected from the group consisting of
(R)-2-[3,5-cis-3-(3-Fluoro-phenyl)-5-methyl-2-oxo-4-(quinolin-6-yl-acetyl)-[1,4]diazepan-1-yl]-3-naphthalen-1-yl-propionamide,
(R)-2-[3,5-cis-5-Methyl-2-oxo-4-(quinolin-6-yl-acetyl)-3-(3-trifluoromethyl-phenyl)-[1,4]-diazepan-1-yl]-3-naphthalen-1-yl-propionamide,
(R)-2-[3,5-cis-3-(4-Fluoro-phenyl)-5-methyl-2-oxo-4-(quinolin-6-yl-acetyl)-[1,4]diazepan-1-yl]-3-naphthalen-1-yl-propionamide,
(R)-2-[3,5-cis-3-(2-Fluoro-phenyl)-5-methyl-2-oxo-4-(quinolin-6-yl-acetyl)-[1,4]diazepan-1-yl-3-naphthalen-1-yl-propionamide,
2-[3,5-cis-3-(3-Bromo-phenyl)-5-methyl-2-oxo-4-(2-quinolin-6-yl-acetyl)-[1,4]diazepan-1-yl-3-naphthalen-1-yl-propionamide,
2-[3-Biphenyl-3-yl-5-methyl-2-oxo-4-(2-quinolin-6-yl-acetyl)-[1,4]diazepan-1-yl]-3-naphthalen-1-yl-propionamide,
(R)-2-[(3S,5R)-3-(3-Chloro-phenyl)-5-methyl-2-oxo-4-(2-quinolin-6-yl-acetyl)-[1,4]diazepan-1-yl]-3-naphthalen-1-yl-propionamide,
(R)-2-[(3S,5R)-3-(3,5-Dichloro-phenyl)-5-methyl-2-oxo-4-(2-quinolin-6-yl-acetyl)-[1,4]diazepan -1-yl-3-naphthalen-1-yl-propionamide,
(R)-2-[(3S,5R)-3-(4-Chloro-3-trifluoromethyl-phenyl)-5-methyl-2-oxo-4-(2-quinolin-6-yl-acetyl)-[1,4]diazepan-1-yl]-3-naphthalen-1-yl-propionamide,
(R)-2-[(3S,5R)-3-(3-Chloro-4-fluoro-phenyl)-5-methyl-2-oxo-4-(2-quinolin-6-yl-acetyl)-[1,4]diazepan-1-yl]-3-naphthalen-1-yl-propionamide,
(R)-2-[(3S,5R)-5-Methyl-2-oxo-4-(2-quinolin-6-yl-acetyl)-3-(2-trifluoromethyl-phenyl)-[1,4]diazepan-1-yl]-3-naphthalen-1-yl-propionamide.
(R)-2-[(3S,5R)-3-(3,4-Difluoro-phenyl)-5-methyl-2-oxo-4-(2-quinolin-6-yl-acetyl)-[1,4]diazepan -1-yl]-3-naphthalen-1-yl-propionamide, (R)-2-[(3S,5R)-3-(3-Cyano-phenyl-5-methyl-2-oxo-4-(2-quinolin-6-yl-acetyl)-[1,4]diazepan-1-yl]-3-naphthalen-1-yl-propionamide, (R)-2-[5-Methyl-2-oxo-3-(3-pyrimidin-5-yl-phenyl)-4-(2-quinolin-6-yl-acetyl)-[1,4]diazepan-1-yl]-3-naphthalen-1-yl-propionamide, (R)-2-[(3S,5R)-5-Methyl-2-oxo-4-(2-quinolin-6-yl-acetyl)-3-(3-trifluoromethoxy-phenyl)-[1,4]diazepan-1-yl]-3-naphthalen-1-yl-propionamide, (R)-2-[4-(2-Benzo[1,3]dioxol-5-yl-acetyl)-3,5-cis-3-(3-fluoro-phenyl)-5-methyl-2-oxo-[1,4]diazepan-1-yl]-3-naphthalen-1-yl-propionamide, (R)-2-[(3S,5R)-4-(2-Benzo[1,3]dioxol-5-yl-acetyl)-3-(3-chloro-phenyl)-5-methyl-2-oxo-[1,4]diazepan-1-yl]-naphthalen-1-yl-propionamide, (R)-2[(3S,5R)-4-(2-Benzo[1,3]dioxol-5-yl-acetyl)-5-methyl-2-oxo-3-(3-trifluoromethyl-phenyl)-[1,4]diazepan-1-yl]-3-naphthalen-1-yl-propionamide, (R)-2-[(3S,5R)-4-(2-Benzo[1,3]dioxol-5-yl-acetyl)-3-(3-chloro-4-fluoro-phenyl)-5-mehtyl-2-oxo-[1,4]diazepan-1-yl]-3-naphthalen-1-yl-propionamide, (R)-2-[(3S,5R)-4-(2-Benzo[1,3]dioxol-5-yl-acetyl)-3-(3-cyano-phenyl)-5-methyl-2-oxo-[1,4]diazepan-1-yl]-3-naphthalen-1-yl-propionamide, (R)-2-[(3S,5R)-4-(2-Benzo[1,3]dioxol-5-yl-acetyl)-5-methyl-2-oxo-3-(3-trifluoromethoxy-phenyl)-[1,4]diazepan-1-yl]-3-naphthalen-1-yl-propionamide, (R)-2-[(3S,5R)-3-(3-Chloro-phenyl)-5-methyl-2-oxo-4-phenylacetyl-[1,4]diazepan-1-yl]-3-naphthalen-1-yl-propionamide, (R)-2-{3,5-cis-3-(3-Fluoro-phenyl)-5-methyl-2-oxo-4-[(3-trifluoromethyl-phenyl)-acetyl]-[1,4]diazepan-1-yl}-3-naphthalen-1-yl-propionamide, 3,5-cis-2-{3-Biphenyl-4-yl-5-methyl-2-oxo-4-[2-(2,3,6-trichloro-phenyl)-acetyl]-[1,4]diazepan-1-yl}-3-naphthalen-1-yl-propionamide, (R)-2-[(3S,5R)-4-[2-(4-Cyano-phenyl)-acetyl]-3-(3,4-difluoro-phenyl)-5-methyl-2-oxo-[1,4]diazepan-1-yl]-3-naphthalen-1-yl-propionamide, (R)-2-[(3S,5R)-3-(3-Chloro-phenyl)-4-[2-(4-cyano-phenyl)-acetyl]-5-methyl-2-oxo-[1,4]diazepan-1-yl]-3-naphthalen-1-yl-propionamide, (R)-2-[(3S,5R)-4-[2-(4-Amino-phenyl)-acetyl]-3-(3-chloro-phenyl)-5-methyl-2-oxo-[1,4]diazepan-1-yl]-3-naphthalen-1-yl-propionamide, (R)-2-[(3S,5R)-4-[2-(4-Amino-phenyl)-acetyl]-5-methyl-2-oxo-3-(3-trifluoromethyl-phenyl)-[1,4]diazepan-1-yl]-3-naphthalen-1-yl-propionamide, (R)-2-[(3S,5R)-4-[2-(4-Dimethylamino-phenyl)-acetyl]-5-methyl-2-oxo-3-(3-trifluoromethyl-phenyl)-[1,4]diazepan-1-yl]-3-naphthalen-1-yl-propionamide, (R)-2-[(3S,5R)-4-[2-(3-Amino-phenyl)-acetyl]-3-(3-chloro-phenyl)-5-methyl-2-oxo-[1,4]diazepan-1-yl]-3-naphthalen-1-yl-propionamide, N-(4-{2-[(2S,7R)-4-((R)-1-Carbamoyl-2-naphthalen-1-yl-ethyl)-7-methyl-3-oxo-2-(3-trifluoromethyl-phenyl)-[1,4]diazepan-1-yl]-2-oxo-ethyl}-phenyl)-succinamic acid, N-(4-{2-[4-(1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-succinamic acid, N-(3-{2-[4-(1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-succinamic acid, (R)-2-[(3S,5R)-4-{2-[4-(2-Amino-acetylamino)-phenyl]-acetyl}-3-(3-chloro-phenyl)-5-methyl-2-oxo-[1,4]diazepan-1-yl]-3-naphthalen-1-yl-propionamide, (R)-2-[(3S,5R)-4-{2-[3-(2-Amino-acetylamino)-phenyl]-acetyl}-3-(3-chloro-phenyl)-5-methyl-2-oxo-[1,4]diazepan-1-yl]-3-naphthalen-1-yl-propionamide, (R)-2-[(3S,5R)-4-{2-[4-(2-Amino-propionylamino)-phenyl]-acetyl}-3-(3-chloro-phenyl)-5-methyl-2-oxo-[1,4]diazepan-1-yl]-3-naphthalen-1-yl-propionamide, N-(4-{2-[4-((R)-1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-acrylamide, N-(4-{2-[(2S,7R)-4-((R)-1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-4-morpholin-4-yl-4-oxo-butyramide, N-(4-{2-[(2S,7R)-4-((R)-1-Carbamoyl-2-naphthalen-1-yl-ethyl)-2-(3-chloro-phenyl)-7-methyl-3-oxo-[1,4]diazepan-1-yl]-2-oxo-ethyl}-phenyl)-4-oxo-4-piperazin-1-yl-butyramide, (R)-2-{(3S,5R)-3-(3-Chloro-phenyl)-4-[2-(2-methoxy-phenyl)-acetyl]-5-methyl-2-oxo-[1,4]diazepan-1-yl}-3-naphthalen-1-yl-propionamide, (R)-2-{(3S,5R)-3-(3-Chloro-phenyl)-4-[2-(2-methoxy-phenyl)-acetyl]-5-methyl-2-oxo-[1,4]diazepan-1-yl}-3-naphthalen-1-yl-propionamide, (R)-2-[(3S,5R)-4-[2-(3-Chloro-methoxy-phenyl)-acetyl]-(3-(3-chloro-phenyl)-5-methyl-2-oxo-[1,4]diazepan-1-yl]-3-naphthalen-1-yl-propionamide, and (R)-2-[(3S,5R)-4-Acetyl-3-(3-chloro-phenyl)-5-methyl-2-oxo-[1,4]diazepam-1-yl]-3-naphthalen-1-yl propionamide.

11. A pharmaceutical composition of claim 6 wherein the other pharmaceutical active agent is selected from cyclosporins, rapamycins ascomycins, corticosteroids, cyclophosphamide, azathioprene, methotrexate, FTY 720, leflunomide, mizoribine, mycophenolic acid, mycophenolate mofetil, 15-deoxyspergualine, immunosuppressive monoclonal antibodies, selectin antagonists or VLA-4 antagonists.

12. A method pharmaceutical composition according to claim 11 wherein the other pharmaceutical active agent is cyclosporin A, cyclosporine G, FK506, ASM981, or monoclonal antibodies to MHC, CD2, CD3, CD4, CD7, CD25, CD28, B7, CD40, CD45, CD58 or their ligands.

13. A method according to claim 8 wherein the other pharmaceutical active agent is selected from cyclosporins, rapamycins ascomycins, corticosteroids, cyclophosphamide, azathioprene, methotrexate, FTY 720, leflunomide, mizoribine, mycophenolic acid, mycophenolate mofetil, 15-deoxyspergualine, immunosuppressive monoclonal antibodies, selectin antagonists or VLA-4 antagonists.

14. A method according to claim 13 wherein the other pharmaceutical active agent is cyclosporin A, cyclosporine G, FK506, ASM981, or monoclonal antibodies to MHC, CD2, CD3, CD4, CD7, CD25, CD28, B7, CD40, CD45, CD58 or their ligands.

15. The composition of claim 5 wherein the compound is the compound of claim 2.

16. The composition of claim 5 wherein the compound is the compound of claim 3.

17. The composition of claim 5 wherein The compound is the compound of claim 9.

18. The composition of claim 5 wherein the compound is the compound of claim 10.

19. The method of claim 7 wherein the compound is the compound of claim 2.

20. The method of claim 7 wherein the compound is the compound of claim 3.

21. The method of claim 7 wherein the compound is the compound of claim 9.

22. The method of claim 7 wherein the compound is the compound of claim 10.

* * * * *